US009408782B2

(12) United States Patent
Wong et al.

(10) Patent No.: US 9,408,782 B2
(45) Date of Patent: Aug. 9, 2016

(54) ORTHODONTIC ADHESIVES

(71) Applicant: Ormco Corporation, Orange, CA (US)

(72) Inventors: Raymond F. Wong, Chino Hills, CA (US); Kevin Corcoran, Corona, CA (US)

(73) Assignee: Ormco Corporation, Orange, CA (US)

( * ) Notice: Subject to any disclaimer, the term of this patent is extended or adjusted under 35 U.S.C. 154(b) by 3 days.

(21) Appl. No.: 14/445,815

(22) Filed: Jul. 29, 2014

(65) Prior Publication Data

US 2014/0336297 A1   Nov. 13, 2014

Related U.S. Application Data

(63) Continuation of application No. 13/618,722, filed on Sep. 14, 2012, now Pat. No. 8,821,157, which is a continuation of application No. 11/750,764, filed on May 18, 2007, now abandoned.

(51) Int. Cl.
  *A61K 6/083* (2006.01)
  *A61K 6/00* (2006.01)
  *A61K 6/09* (2006.01)

(52) U.S. Cl.
  CPC ............... *A61K 6/083* (2013.01); *A61K 6/0023* (2013.01); *A61K 6/0052* (2013.01); *A61K 6/0064* (2013.01); *A61K 6/09* (2013.01)

(58) Field of Classification Search
  USPC ................................ 523/116, 118; 522/18, 33
  See application file for complete search history.

(56) References Cited

U.S. PATENT DOCUMENTS

| | | | |
|---|---|---|---|
| 4,554,336 A | 11/1985 | Kidd et al. | |
| 4,668,666 A | 5/1987 | Allan et al. | |
| 4,735,632 A | 4/1988 | Oxman et al. | |
| 4,792,632 A | 12/1988 | Ellrich et al. | |
| 5,348,475 A | 9/1994 | Waknine et al. | |
| 5,354,199 A | 10/1994 | Jacobs et al. | |
| 5,362,769 A | 11/1994 | Waller et al. | |
| 5,468,801 A | 11/1995 | Antonelli et al. | |
| 5,545,676 A | 8/1996 | Palazzotto et al. | |
| 5,596,025 A | 1/1997 | Oxman et al. | |
| 5,684,103 A | 11/1997 | Jia et al. | |
| 6,020,395 A * | 2/2000 | Angeletakis ........... A61K 6/083 428/405 |
| 6,126,922 A | 10/2000 | Rozzi et al. | |
| 6,284,321 B1 | 9/2001 | Brindoepke et al. | |
| 6,362,250 B1 | 3/2002 | Karmaker et al. | |
| 6,387,982 B1 | 5/2002 | Blackwell | |
| 6,528,555 B1 | 3/2003 | Nikutowski et al. | |
| 6,670,436 B2 | 12/2003 | Burgath et al. | |
| 6,899,948 B2 | 5/2005 | Zhang et al. | |
| 6,960,079 B2 | 11/2005 | Brennan et al. | |
| 7,090,721 B2 | 8/2006 | Craig et al. | |
| 7,275,932 B2 | 10/2007 | Jin et al. | |
| 2004/0180983 A1 | 9/2004 | Hara et al. | |
| 2005/0043490 A1 | 2/2005 | Klee et al. | |
| 2005/0123762 A1 | 6/2005 | Ori et al. | |
| 2005/0192374 A1 | 9/2005 | Jia et al. | |
| 2007/0173558 A1 | 7/2007 | Jin et al. | |
| 2007/0197683 A1 | 8/2007 | Jia et al. | |

OTHER PUBLICATIONS

Rashid Ahmed Chamda et al., "Time-Related Bond Strengths of Light-Cured and Chemically Cured Bonding Systems: An in vitro study," American Journal of Orthodontics and Dentofacial Orthopedics, vol. 100, No. 4, 1996.
Daryl Lynden Proctor, "Fracture Properties of Different Orthodontic Bonding Materials", A Thesis, Loma Linda University Graduate School, Jun. 2001.
Optilux 501 Curing Light, Operator's Manual, Kerr Corporation, Sybron Dental Specialties, 15 pages.
Light Bond Manufacturer Instruction and MSDS, Reliance Orthodontic Products, Inc., 3 pages, 2006.
Quick Cure Manufacturer Instruction and MSDS, Reliance Orthodontic Products, Inc., 4 pages, 2009.
Lane et al., Ambient Light Working Times of Visible Light-Cured Restorative Material. Does the ISO Standard Reflect Clinical Reality? Dental Materials, Sep. 1998, vol. 14, pp. 353-357.
O'Brien et al., A Visible Light-Activated Direct-Bonding Material: An in Vivo Comparative Study, Am. J. Orthod. Dentofac. Orthhop., Apr. 1989, vol. 94, No. 4, pp. 348-351.
Dlugokinski et al., Assessing the Effect of Extraneous Light on Photoactivated Resin Composites, JADA, Aug. 1998, vol. 129, pp. 1103-1109.
3M Unitek Orthodontic Products, 3M Unitek Transbond XT Light Cure Orthodontic Adhesive in Syringes or Capsules, www.3m.com, 2008, 4 pages.
3M Unitek Orthodontic Products, 3M Unitek Transbond LR Light Cure Adhesive in Capsules for Bonded Lingual Retainers, www.3m.com, 2005, 2009, 1 page.
3M Unitek, www.3m.com, Transbond XT Light Cure Adhesive, 1 page, 2008.
3M Unitek, www.3m.com, Transbond LR Light Cure Adhesive, 1 page, 2005.
Instructions for Light Bond Orthodontic Bonding System, Bonding Procedure, 1 page, 2005.
Enlight Adhesive Instructions, 1 page.
Section 7.9; Sensitivity to Ambient Light, Class 2 Materials; ISO 4049:2000(E), 2 pages.
European Patent Office, Search Report and Preliminary Opinion issued in corresponding European Application No. EP08251750 dated Sep. 2, 2010, 4 pp.

* cited by examiner

*Primary Examiner* — Tae H Yoon
(74) *Attorney, Agent, or Firm* — Wood, Herron & Evans, LLP

(57) ABSTRACT

An single component light-curable orthodontic adhesive includes a curable resin monomer component; a quaternary curing initiator system; and filler. The orthodontic adhesive has a long working time (W) and short curing time (C). The adhesives are suitable as light-curing and may include a colorant. Suitable colorants include reversible, thermochromic dyes. The adhesive may also include a resin toughening component.

18 Claims, 12 Drawing Sheets

ORTHODONTIC ADHESIVES

RELATED APPLICATIONS

This application is a continuation of U.S. application Ser. No. 13/618,722 filed on Sep. 14, 2012, now U.S. Pat. No. 8,821,157, which is a continuation of U.S. application Ser. No. 11/750,764 filed on May 18, 2007, which is now abandoned, wherein each of the disclosures is incorporated herein by reference in its entirety.

FIELD OF THE INVENTION

The present invention relates to orthodontic adhesives and, in particular, to orthodontic adhesives having extended or increased working times and/or shortened or reduced curing times, resulting in improved work/cure (W/C) ratios. The term "orthodontic" as used herein is intended to include "dental" applications as well as orthodontic applications.

BACKGROUND OF THE INVENTION

Bonding orthodontic appliances (e.g., brackets) onto a patient's teeth requires an adhesive. Light-curable adhesives are most popular due to their single-component nature (i.e., no mixing). As will be appreciated, it is important to bond brackets or other attachments with a high bonding integrity as that translates to the durability and longevity of the bond. Two significant factors in attaining high bonding integrity are long working time and a quick, high-strength cure.

Long working time is essential to accommodate typical clinical dynamics. For example, for direct bonding of orthodontic brackets, there must be enough time to apply the adhesive paste to the bracket base under normal office lighting, then under exam lighting place the bracket on the patient's tooth, seat the bracket and extrude the excess adhesive, clean the excess, re-position the bracket to the final location, and perform a final clean-up. This entire sequence normally takes no longer than 1 minute per bracket. However, as is common, a clinical assistant can do the initial bracket placements while the clinician is performing other duties. In that case, some brackets may remain under high intensity lighting for several minutes. When the clinician does get to final bracket positioning, there is a high probability that the adhesive on some brackets may be long past viable working time and at risk of tearing, void formation, or other polymerization interruption that would result in poor molecular weight growth leading to compromised bond strength. In the worst case, the bracket(s) is rigidly fixed such that final re-positioning is not possible, in which case the entire procedure must be re-started. Compromised bond strength may manifest itself in initial bond failure often before the patient even leaves the office. Or, the bond may hold under initial light-force loadings, but further along in treatment the patient may bite something that would normally not dislodge the bracket, or during wire change the higher forces may cause the bond to fail.

Short cure time is desirable to quickly complete the bonding procedure. Quickly setting the adhesive reduces the overall appointment time thereby benefiting the patient and the clinician. Once the clinician has every bracket or appliance arranged as desired, the adhesive material should be rapid setting, or curing, to acceptable strength levels. This prevents any disturbance or dislocation of the brackets or other appliances, which may then lead to compromised bond strength due to disruption of the adhesive setting/curing reaction. Typical cure times for commercially available adhesives using a dental curing light range from about 10 to 40 seconds.

Currently available light-curable orthodontic adhesives have limits on the working time to curing time ratio (W/C ratio) that is achievable. It is believed that one factor affecting W/C ratios for known orthodontic adhesives is the adhesive initiator system. Some currently available adhesives utilize binary-type (2-component) initiator systems consisting of a sensitizer and an electron donor. One example of such a product is Enlight, available from Ormco Corporation. Other products, such as Transbond XT, available from Unitek/3M Corporation, use a ternary (3-component) initiator system, including a sensitizer, an electron donor, and a third component, an iodonium salt. U.S. Pat. No. 5,545,676 discloses such formulations. Sybron Corporation, in its Sequence product, has utilized a ternary initiator system that includes a sensitizer, an electron donor, and a peroxide catalyst. This initiator system is disclosed in U.S. Pat. No. 5,362,769.

The W/C ratio of orthodontic adhesives is affected by both the duration of the working time (W) of the adhesive and the duration of the curing time (C) of the adhesive. As a point of reference, the W/C ratio for Enlight Adhesive has been determined to be 2. Efforts aimed at improving the speed of curing and the physical properties of hardened adhesives typically have been directed at the curing light source. Improvements to conventional tungsten-quartz halogen bulb filtered light have approached their limit, and use of higher intensity light, such as xenon plasma pulsing or arcing (PAC) lights, have achieved limited success. Also, more monochromatic sources like [Argon] laser, and LED-type curing lights have attempted to match the absorption wavelengths of photoinitiators.

Providing orthodontic adhesives with a greater W/C ratio than currently available products is one of the objects of the present invention. Another objective of the present invention is an improved initiator system. A further objective is to provide orthodontic adhesives with desirable physical properties after curing, including impact toughness.

SUMMARY OF THE INVENTION

To achieve the foregoing objects, and in accordance with the present invention, orthodontic adhesive compositions having W/C ratios of at least 10, 12, 14 and even 20 and higher have been developed. The orthodontic adhesive compositions include a curable resin monomer component, a curing initiator system and filler. Also in accordance with the present invention are orthodontic adhesives, which include a curable resin monomer component, a quaternary curing initiator system and filler. The orthodontic adhesives may further include a colorant and/or a resin toughening component. Furthermore, the curable resin monomer component may include more than one different curable resin monomer. Moreover, the quaternary curing initiator system may include at least two different sensitizers. Adhesives in accordance with the present invention facilitate the successful completion of sometimes difficult, usually long, and routinely delayed bonding procedures in the clinical setting.

BRIEF DESCRIPTION OF THE DRAWINGS

These and other features, aspects, and advantages of the present invention will become better understood with regard to the following description, appended claims and accompanying drawings wherein:

DETAILED DESCRIPTION

The compositions of the present invention have the unique combination of long working times and fast cure times, which results in W/C ratios superior to those of currently-available orthodontic adhesives.

Conventional, state-of-the-art light-cured orthodontic adhesives (dental composites) typically have a working time of about 50 seconds and a cure time of about 20 seconds. The compositions of the present invention may extend the working time up to about 70-100 seconds, under typical examination lighting conditions, and may reduce the cure time to about 5 seconds. Thus, whereas the W/C ratio of current market materials is about 2.5 (and in some instances up to about 8), the W/C ratio of compositions of the invention is at least 10 and may range from about 14-20, or higher. This highly desirable improvement is important for reducing bond failures, as it allows the practitioner to carefully adjust bracket (or other orthodontic appliance) placement under bright ambient lighting due to the increased working time of the adhesive, then fix the bracket in the desired position quickly due to the short cure time of the adhesive, to rapidly achieve high bond strength and bond integrity. The short cure time is also beneficial as it may reduce patient discomfort by up to several minutes, depending on the number of teeth having brackets bonded to them. It also saves the clinician's office time and money as per patient chair time is reduced. Further, the initial bond strength achieved in a short time is higher than typical adhesives such that wire tie-in and other high-force procedures can be accomplished promptly without fear of a bracket de-bond.

Compositions of the present invention may advantageously make use of a quaternary curing initiator system. It is believed that such quaternary curing initiator systems contribute to the achievement of the superior W/C ratios in the adhesive compositions of the invention. As used herein, the term "quaternary" (quat) is intended to mean initiator systems having four or more components.

Figure 1:
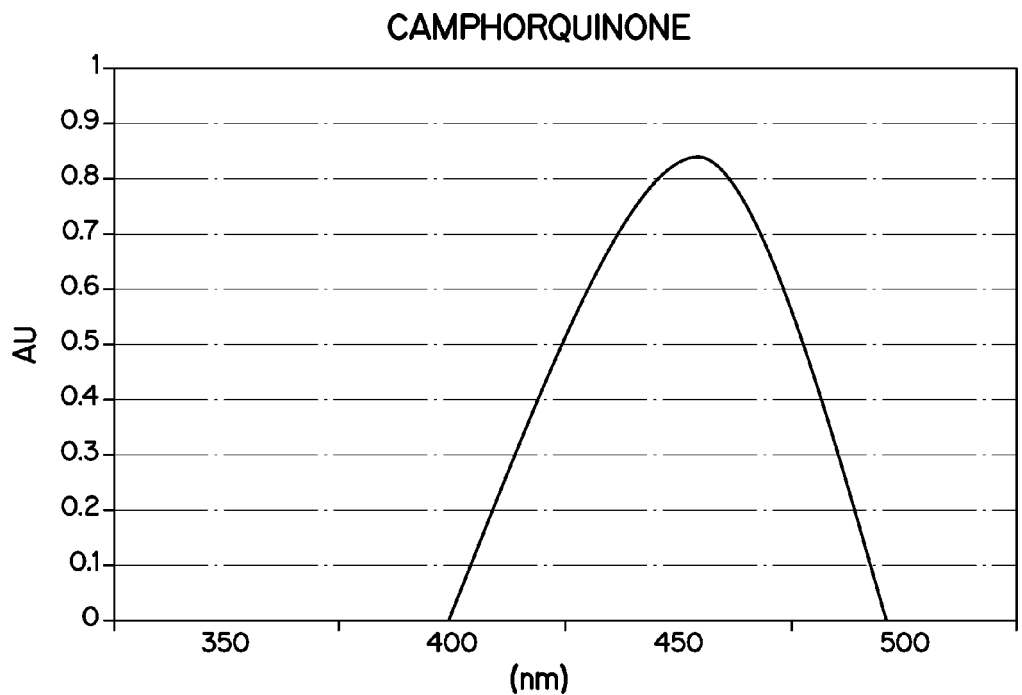
FIG. 1 is a graphical representation of the wavelength absorption spectra for camphorquinone (CQ)
Figure 3:
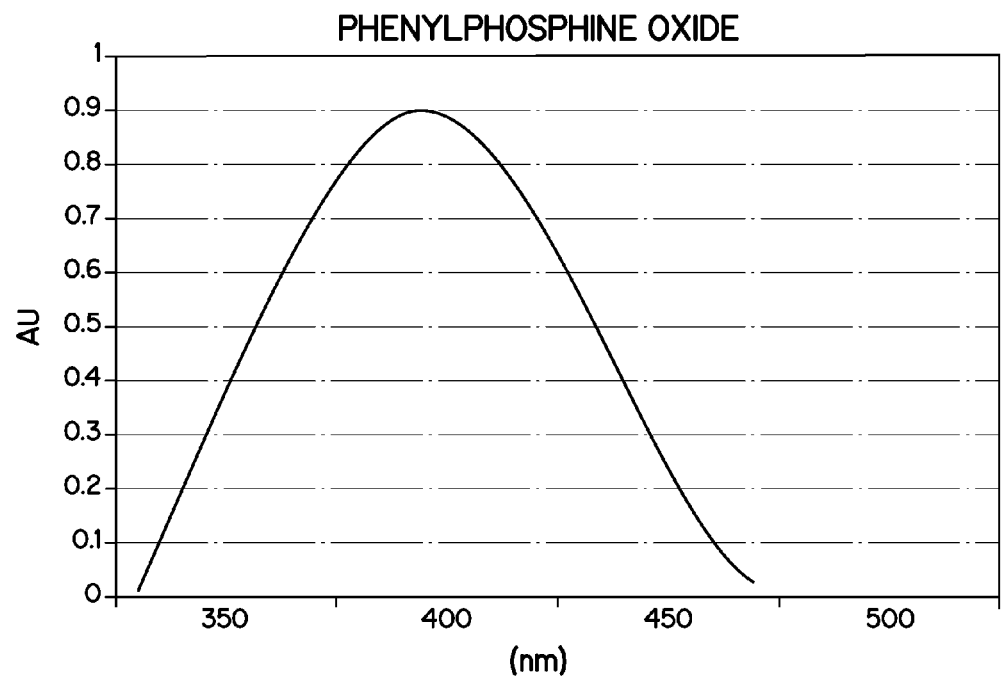
FIG. 3 is a graphical representation of the wavelength absorption spectra for phenylphosphine oxide (PPO)
Figure 4:
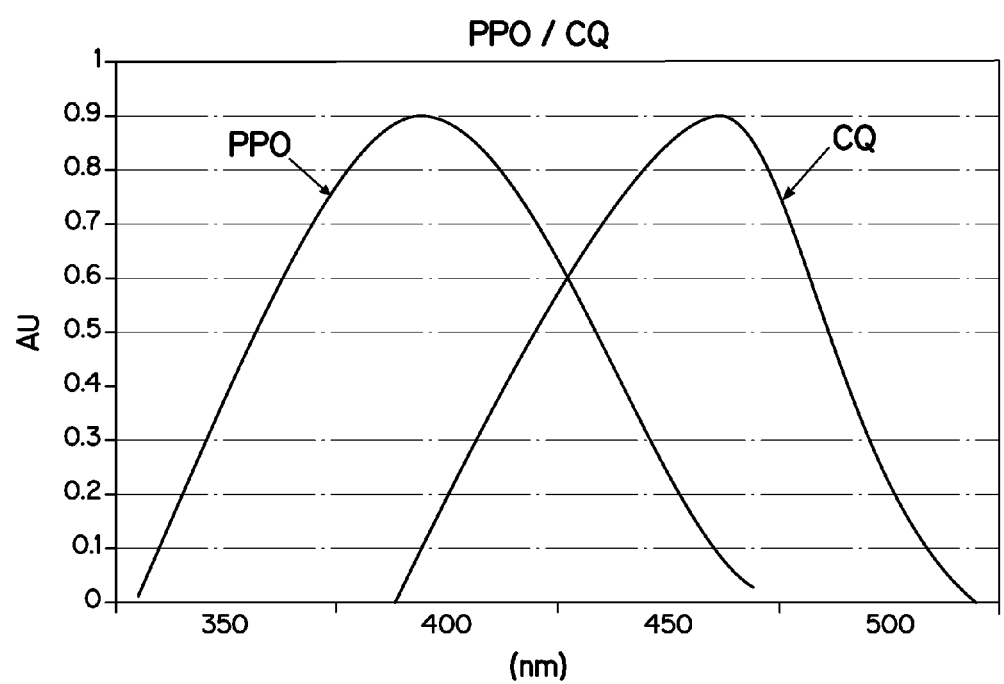
FIG. 4 is a graphical overlay of the absorption spectra for PPO and CQ.

In one embodiment, the initiator system includes at least two sensitizers, an electron donor, and a catalyst. Advantageously, an exemplary composition may include two sensitizers having different absorption maximas. Two examples of such sensitizers are phenylphosphine oxide (PPO) and camphorquinone (CQ), which have peak absorption at 380 nm and 470 nm, respectively, and overlap in the region between. See FIGS. 1, 3 and 4. Utilizing a curing lamp that puts out blue light in the 350 nm to 520 nm region, an initiator system that includes both PPO and CQ would take advantage of all energy available and results in shorter/faster cure times than using either PPO or CQ alone. At the same time, this combination of sensitizers is not particularly sensitive under ambient lighting conditions in the clinical setting, thus enhancing the working time.

By way of example, under typical clinical examination lighting conditions of 10,000 lux, an exemplary composition of the present invention (identified as Composition A in the FIGS.) can achieve W/C ratios in excess of 30. Under 10,000 lux exam light, the W/C ratio is calculated as seconds of working time/seconds of cure time. See FIG. 9, which compares the W/C ratio for Composition A of the present invention with that of Quick, available from Reliance Orthodontic Products Corporation, Ormco Corporation's Enlight, Light Bond from Reliance, and Transbond XT from Unitek/3M Corporation.

Under common office fluorescent lighting conditions (400 lux), the ratio is expressed in minutes of working time/seconds of cure time and the inventive materials achieve W/C ratios on the order of 30, while known adhesives achieve W/C ratios in the range of 0.5 to 3. See FIG. 10.

As stated, adhesives of the present invention having improved W/C ratios may advantageously utilize a multi-sensitizer ["quaternary curing"] initiator system. There are many known sensitizers used for light initiated polymerization of acrylic resins such as dental and orthodontic materials, including adhesives. However, probably the most universally employed sensitizer for commercial dental and orthodontic products is camphorquinone (CQ). In conjunction with an electron donor, a binary initiator system that includes CQ satisfactorily converts acrylic monomers to a generally crosslinked polymeric matrix by way of a dental/orthodontic curing light. Dental/orthodontic curing lights (hereinafter "dental curing lights" or "curing lights") generally have wavelength output in the 300 to 550 nanometer (nm) range. The resultant hardened composite resin is useful for many dental and orthodontic applications. A ternary initiator system represents an improvement over the binary type. One such system is disclosed in U.S. Pat. No. 5,545,676 that includes an iodonium salt in addition to the CQ and electron donor. It appears that addition of the iodonium salt aids production of free radicals during high intensity light curing. Most likely, this improved efficiency allows the concentration of CQ to be reduced, thus the working time is modestly extended. Another ternary system is disclosed in U.S. Pat. No. 5,362,769. Again, this system uses the traditional CQ/electron donor, and includes a peroxide that decomposes to free radicals at a rate corresponding to the thermal conditions. The specific peroxide is chosen appropriately for decomposition/free radical production at body temperature. Thus, materials using this type of curing system will gain strength over time as the polymerization drives to completion due to the latent curing effect.

Figure 2:
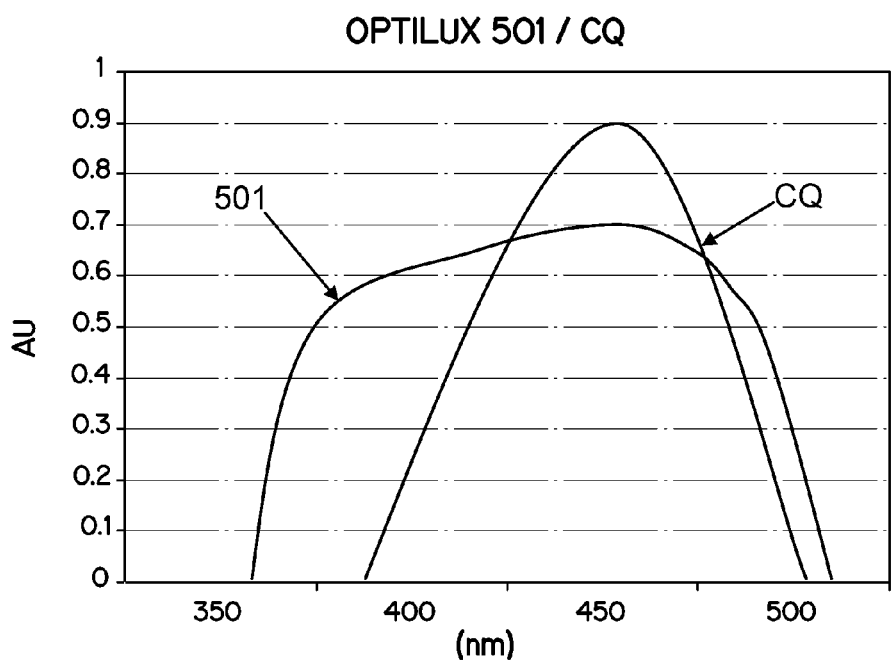
FIG. 2 is a graphical representation of the light output from an Optilux 501 light source overlaid on the absorption spectra of FIG. 1.

Both known binary and ternary systems typically use only one sensitizer. Sensitizers generally are wavelength specific, e.g., CQ has maximum absorption at 470 nm, and falls off rapidly to either side within 50 nm. See FIG. 1. Thus, single sensitizer systems do not take full advantage of the available light energy of a typical dental curing light. FIG. 2 depicts this as an overlay of the light output from a Demetron Optilux 501 halogen curing light on the wavelength absorption spectra for CQ.

There are many known UV photoinitiators/sensitizers, however these have generally not been employed in curing dental or orthodontic compositions because the tooth structure attenuates the UV light resulting in a sluggish setting reaction. Thus, the depth of cure (degree of monomer to polymer conversion) and corresponding composite strength are limited. Some UV photoinitiators/sensitizers having absorption maxima at higher (near UV) wavelengths are of interest because the energy output of typical dental curing lights in the upper UV A region is high enough to be useful. The family of phosphine oxides is very active and efficient photoinitiators or sensitizers for dental acrylic resin polymerization. U.S. Pat. No. 4,792,632, the disclosure of which is incorporated herein by reference, describes the use of such photoinitiators. A particularly useful photoinitiator/sensitizer for use with a dental curing light is phenylbis(2,4,6-trimethylbenzoyl)phosphine oxide (PPO) because it has an absorption maximum at 390 nm. See FIG. 3.

Figure 5:
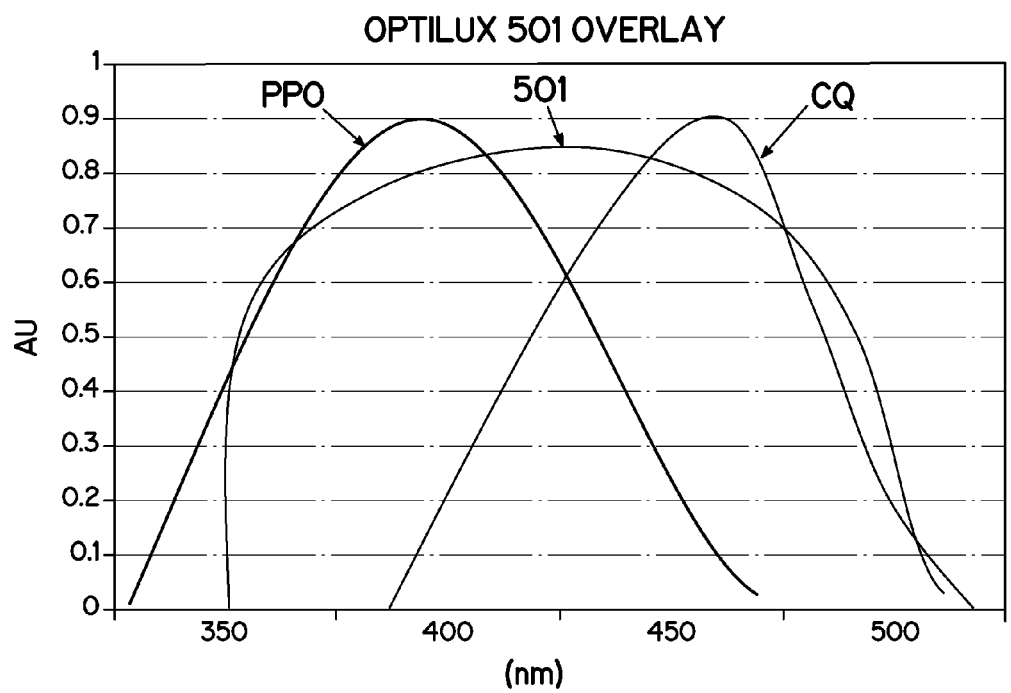
FIG. 5 is a graphical overlay of the light output from an Optilux 501 light source on the absorption spectra of PPO and CQ of FIG. 4.

It has advantageously been determined that by combining PPO with a typical visible light dental resin initiator/sensitizer, i.e., CQ, the resin composition sensitivity in the dental curing light spectrum is significantly enhanced. See FIGS. 4 and 5. It has further been determined that by lowering the concentration of CQ and maintaining a relatively high concentration of PPO, the ambient light working time for adhesive compositions containing this dual sensitizer combination can be significantly increased.

There are a wide variety of colorants or dyes known in the field of dental and orthodontic adhesives. Selection of a proper colorant (or colorants), and the associated color changing mechanism, is another aspect of the present invention. One useful feature of colorants used in the compositions of the present invention is to provide a visual aid that helps the clinician during clean-up of excess adhesive after initial bonding, and any adhesive remnants at the end of treatment when the bracket is de-bonded. More particularly, it is advantageous to utilize one or more colorants that impart a color to the adhesive which contrasts with the tooth color. Moreover, the proper choice of colorant may further improve the W/C. By way of example, U.S. Pat. Nos. 5,596,025 and 6,528,555 provides a list of dyes and colorants that may be useful for the present invention. U.S. Pat. No. 6,670,436 discloses several thermochromatic color changing compounds. There is no limitation to the type of irreversible or reversible types of colorants, and there are other more conventional types that are contemplated to improve the W/C, e.g., FD&C organic and inorganic pigments such as the blue and green colored aluminum lake compounds.

The adhesive compositions of the present invention may incorporate a color changing reversible thermochromatic dye that deeply colors the composition below its clearing temperature, and turns tooth colored via a reversible mechanism above the clearing temperature. As briefly noted above, a contrasting color is a significant and desirable advantage over currently available commercial adhesive materials for two main reasons: (1) the colorant serves as a visual aid to help clean-up extraneous adhesive during the initial bonding procedure; and (2) the colorant serves as a visual aid to help clean-up adhesive remnant following de-bracketing at the end-of-treatment procedure. At initial bonding and during placement of the appliance (bracket), the proper technique is to lightly force the bracket into position, completely filling the under-pad area with void-free adhesive and allowing the excess to extrude around the periphery of the bonding pad. This insures a maximum mass of adhesive between the pad and the tooth for the highest bond integrity, and the least chance of voids, especially at the margins, otherwise that could lead to food traps and enamel decay. Eliminating voids also reduces the likelihood of stress risers where a bond failure could initiate. Completely removing this "flash" remnant during the clean-up is simplified due to the highly contrasting color. It is critical prior to permanent setting (light curing) so that there is minimal extraneous material that would be detrimental to good hygiene, i.e., food and plaque trap/attachment sites. Conventional adhesives that are tooth colored or transparent are very difficult to clean-up due to the poor visual contrast. At the end-of-treatment de-bracket appointment, the clinician is faced with the same concern of scrupulously cleaning the teeth, this time free of polymerized (hardened) adhesive remnant. Fortunately the correctly chosen colorant is indifferent to a monomer or polymeric matrix, so that after bracket removal, if the remnants of the inventive adhesive can be cooled by, e.g., water and air spray, below their clearing temperature, deep color returns, and remnant becomes highly visible. This facilitates clean-up by, e.g., manual scraping and/or a high-speed handpiece. Thus patient hygiene and tooth appearance is improved.

During treatment, when at body temperature and above the colorant clearing temperature, the adhesive is generally tooth colored. In the case where the mouth may be cold (e.g., when eating ice cream) the colorant mechanism may reverse, and color of the adhesive could be noticeable, particularly under clear brackets. However, for applications where the inventive adhesive materials are used with metal brackets, any color change is generally hidden, and in any event the adhesive color will revert to clear/tooth colored in short order as the temperature rises above the clearing temperature. In the case of clear brackets, the color hue and concentration are carefully chosen to maximize contrast when required, but minimize the obviousness of color reversion under bonded brackets. Examples of reversible, thermochromic colorants that are particularly useful in the compositions of the present invention are leuco dyes available from Color Change Corp. The clearing temperature and particular color of the leuco dyes may be chosen from a wide assortment of stock or custom formulations.

Figure 6:
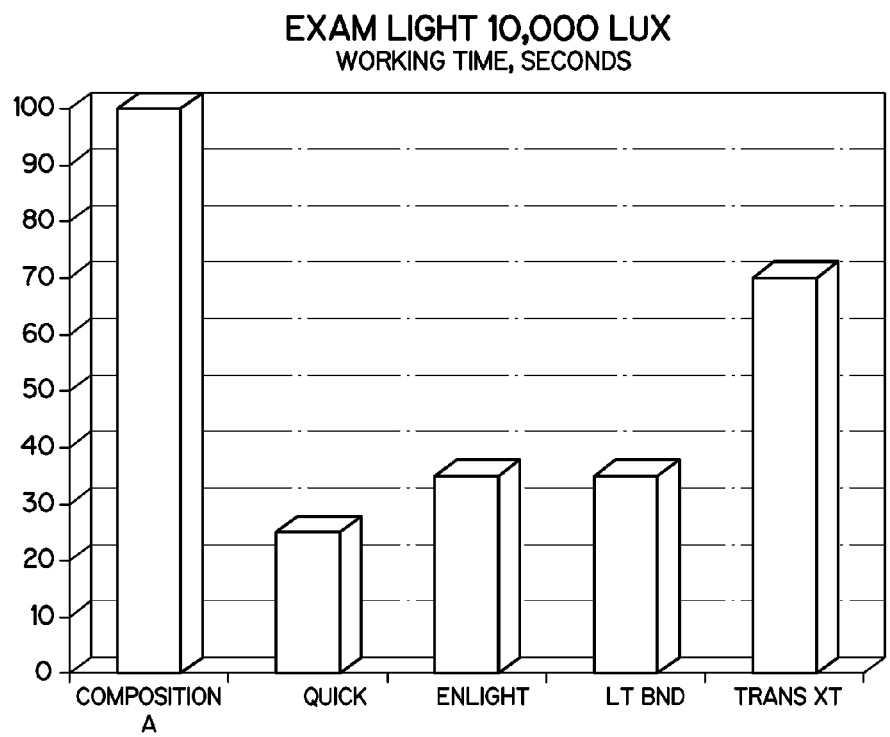
FIG. 6 is a bar graph comparison of the working times (in seconds) for various orthodontic adhesive compositions, including Composition A of the present invention, in the presence of a 10,000 lux light source.
Figure 7:
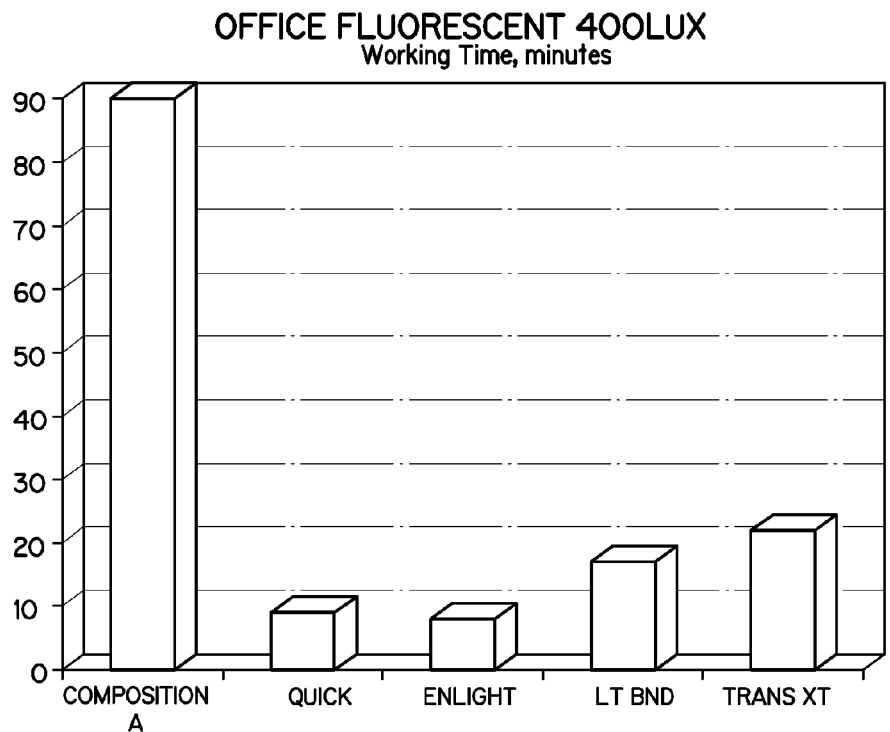
FIG. 7 is a bar graph comparison of the working times (in minutes) for various orthodontic adhesive compositions in the presence of a 400 lux light source.

FIGS. 6 and 7 illustrate the improved working times of an exemplary composition of the present invention (Composition A) versus currently available orthodontic adhesive products (identified by their trade names). For comparative purposes, the working time was noted as the point at which the paste-like characteristic of the adhesive sufficiently hardened to a crusty-like consistency, rounded to the nearest 5-second interval. This test is industry-specific for the dental/orthodontic industry, not one universally recognized, and closely represents the actual circumstances experienced in the clinical environment. A defined lighting condition was prepared; for chair examination lighting, a Belmont® brand (model HLW, Belmont Equipment Corporation, Japan) halogen operatory exam lamp was positioned at a distance (approximately 23") that provided 10,000 lux output at the test site. The lux, a measure of the photon flux, or light density, was read directly by a Minolta illuminance meter, (model T-10, Minolta Company, Ltd, Japan). The working time as shown in FIG. 6 for exam lighting was measured in seconds. For office lighting (fluorescent, 400 lux), the reading of the light meter at normal table height was recorded. As shown in FIG. 7, the working time was measured in minutes.

The data depicted in FIGS. 6 and 7 was compiled by taking an extruded paste sample for each adhesive approximately 2 mm in width×2 mm in depth×20 mm in length from a syringe package onto a clear glass microscope slide in non-actinic lighting conditions. A standard white paper was placed at the test site to standardize the background. The sample on the slide was placed on the white paper at the location of the light meter reading and a stopwatch was started simultaneously. At 10 to 15 seconds (1 to 2 minutes for office fluorescent) prior to the expected working time duration, the sample was cut (like a loaf of bread) in approximately 2 mm sections at approximately 5-second intervals (1 to 5 minute intervals for office fluorescent) until the sample was no longer pasty and had a brittle-like fracture result. The time was noted to the nearest 5 seconds (1 to 5 minutes for office fluorescent) as the working time.

An alternative work time test method could be employed utilizing an "Oscillating Rheometer" (Sabri Dental Enterprises, Inc., Downers Grove, Ill.). That device has a needle that vibrates at a preset frequency, and an adjustable heating chamber. In use, a sample would be maintained under non-actinic radiation conditions, and placed in the chamber and equilibrated to the desired test temperature. The needle would then be inserted in the paste at a predetermined depth. When the test button is activated, simultaneously the needle begins to oscillate, an x-y recording device (Linseis model L200E, Princeton Junction, N.J.) starts, and an operatory examination light (Belmont Dental Light) that is positioned at a distance from the sample such that 10,000+/−50 lux (Minolta Iluminance Meter) of light energy is impinging on the sample turns on. The resultant output would appear as an arrowhead-like graph, similar to what a seismograph looks like. The point of flat-line would be taken as the working time. This procedure was not specifically used in testing compositions of the present invention, but is envisioned to be another manner of more "instrumented" nature for determining working time.

With regard to cure time, bond testing is a direct assessment of the adhesive characteristic of importance in the materials of the present invention. Bond testing quantifies the clinical property that is most typically responsible for brackets coming loose. In other words, bond testing measures the amount of cure time necessary to effect adequate clinical bond strengths, which have well-known and accepted minimum threshold values. While it is the most objective and primary test, there are many other methods to express the cure time as a function of strength without departing from the scope of the invention. For example, tensile strength, compressive strength, shore hardness, and depth of cure as a function of light time may be used to supplement the bond strength data.

A fast, immediate high strength cure is important in the context of orthodontic adhesives. Fast, i.e., rapid, conversion of monomer to polymer, sets the bracket so that there is no movement during the build up of strength. Virtually all state-of-the-art orthodontic adhesives set fast (known as "tacking"), but the majority require several additional seconds of light curing to build up strength (high degree of conversion). During this time it is quite possible to inadvertently bump the bracket, e.g., with the dental light guide tip during curing, particularly if the patient twitches there could be contact with the bracket resulting in the probability of compromised bond strength. Depending on the bond strength at any given moment during strength build-up, a physical disruption may disconnect the ability to attain a high maximum final strength.

It is believed that a shear bond strength (SBS) of 6-8 MPa is a clinically acceptable threshold value, as is commonly referenced (Reynolds I R. A review of direct orthodontic bonding. Br J Orthod 2:171-78, 1975.) Virtually all of the commercially available adhesives will fully cure to satisfy this condition. However, very few provide this strength immediately following a relatively short duration of light cure, particularly when used underneath a metallic article that has the tendency to shadow a portion of the adhesive. It has been discovered that most materials require more than 15 seconds of cure time to reach 7 MPa within 60 seconds after light curing, including the three top selling materials, 3M Transbond XT, Reliance Light Bond, and Ormco Enlight. See FIG. 8.

Figure 8:
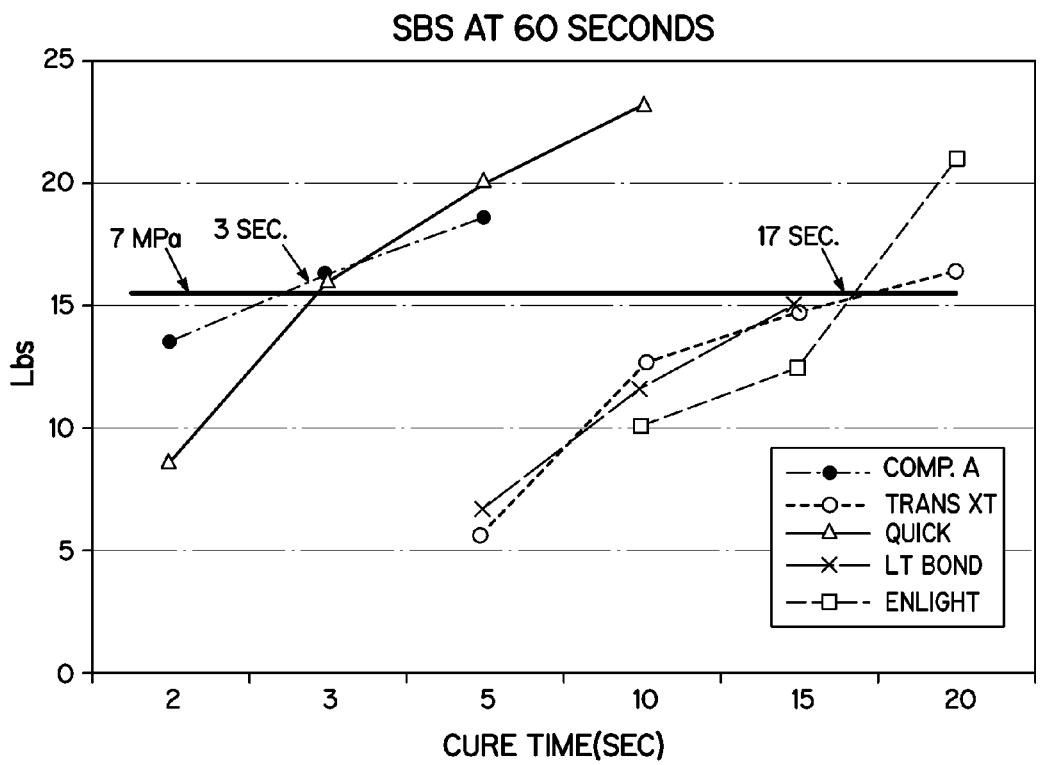
FIG. 8 is a graph of the shear bond strength (SBS) as a function of curing time for various orthodontic adhesive compositions.
Figure 9:
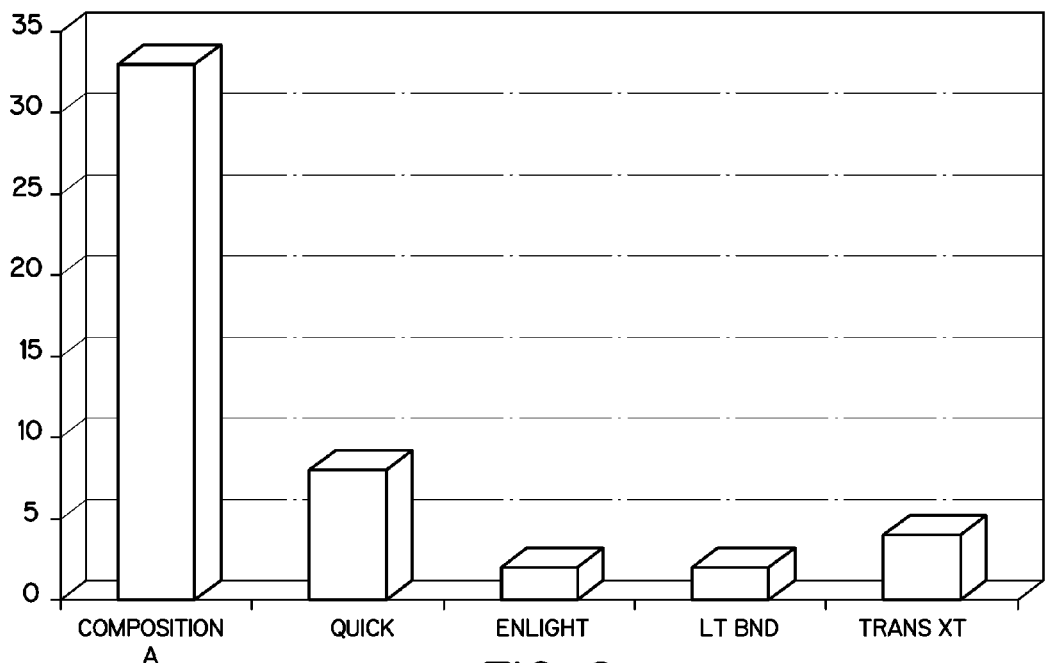
FIG. 9 is a bar graph comparing the W/C ratio for various orthodontic adhesive compositions in the presence of a typical examination light at 23"
Figure 10:
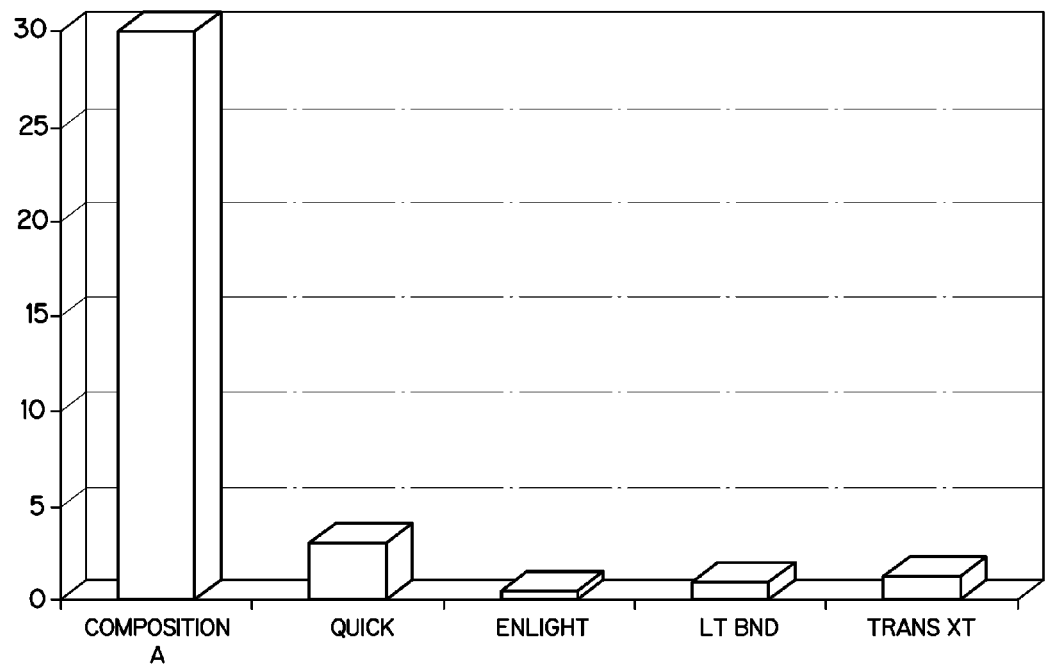
FIG. 10 is a bar graph comparing the W/C ratio for various orthodontic adhesive compositions in the presence of standard office fluorescent lighting at 7'.

To determine the immediate SBS, bovine teeth were encapsulated in acrylic blocks with their facial surface exposed. The teeth were cleaned with pumice, then etched with 37% phosphoric acid for 30 seconds, rinsed and dried with clean compressed air. Ormco Ortho Solo sealant was sparingly applied to the etched and dry enamel. Adhesives were tested using Ormco Orthos Mini Diamond brackets, part number 454-0211 which has a bonding base area of 9.7 mm$^2$. The adhesive was dispensed onto the bracket base, immediately positioned with light force on the sealed tooth, excess "flash" was removed, the bracket was firmly seated with slight repositioning, final flash clean-up, and immediately light cured using a Demetron Optilux 501 (120V AC corded halogen dental curing light, Kerr Corporation) fitted with an 11 mm light guide having output 850 mW/cm$^2$. Each test sample was immediately placed in a holding fixture that oriented the bracket bonded surface in the direction that would be parallel to applied force. The fixture was placed in an Instron model 4467 physical test machine (Instron Corporation, Canton, Mass.), fitted with appropriate compression fixture, and shear force was applied via the bracket tie wings at a rate of 1 mm/minute. When the bracket dislodged the maximum SBS was reported. Each test was completed within 60 seconds following light cure. FIG. 8 shows the results of these tests. As shown, Composition A of the present invention achieved the minimum threshold bond strength needing only very short cure time of 3 seconds. Reliance Quick Cure sets fast to high strength, but has very limited popularity due to its unfriendly short working time (previously illustrated in FIGS. 6 and 7), and therefore poor W/C character (FIGS. 9 and 10). The behavior of Quick Cure is exactly what would be expected for a "hot" (overloaded CQ) poorly balanced binary composition.

The importance of "immediate bond strength" cannot be overstated. Assuming the appliance has been positioned properly and within the working time window such that the adhesive is not compromised in any manner, fast curing to acceptable bond strength (>6 MPa) is critical for the greatest chance of retention throughout the treatment period, which can last for several months or years. In addition to the aforementioned possibility of inadvertent contact during the placement and curing of brackets around the arch, it is routine procedure for the practitioner to place light to moderate load on a bonded attachment immediately following light cure. Typically the clinician will place a probe on the attachment within seconds after light cure and wiggle with light force to make sure the adhesive is set. Lack of an immediate de-bond suggests it is safe to move on to higher force procedures. This wiggle test reduces the possibility that the several minutes spent tying in a wire will be wasted due to a "last bracket failure". For example, after bonding orthodontic brackets, an archwire will be inserted in the bracket slots and ligated. Depending on the severity of the malocclusion, the size and degree of engagement of the archwire, and the type of ligature used, the forces can be directionally high (i.e. force vectors are just right for highest probability of dislodging the bracket). After tying the wire into as many as 15 brackets (1 bracket short of one full arch) it is extremely frustrating and costly to have the last bracket pop off necessitating the wire be completely removed to re-bond one bracket. As can be seen in FIG. 8, many available adhesives will reach a satisfactory 7 MPa value, but only the compositions of the present invention and Reliance Quick Cure will achieve it very fast. Not only does the fast cure assure the greatest chance for high integrity bonding, but it also saves chair time both in terms of money savings to the dental office and discomfort to the patient. As many as 32 brackets may be bonded at one sitting so a savings of several minutes is possible.

While all of the leading adhesives set to a hardened mass relatively quickly, only the present invention has the correct balance of sensitizers and catalysts in the initiator system that maintains the long working time and also provides very fast cure time that involves very high monomer to polymer conversion resulting in immediate high strength. By expressing the key characteristics of work and cure times as a ratio (W/C), the formulations of the present invention perform well above existing materials. See FIGS. 9 and 10.

Figure 11:
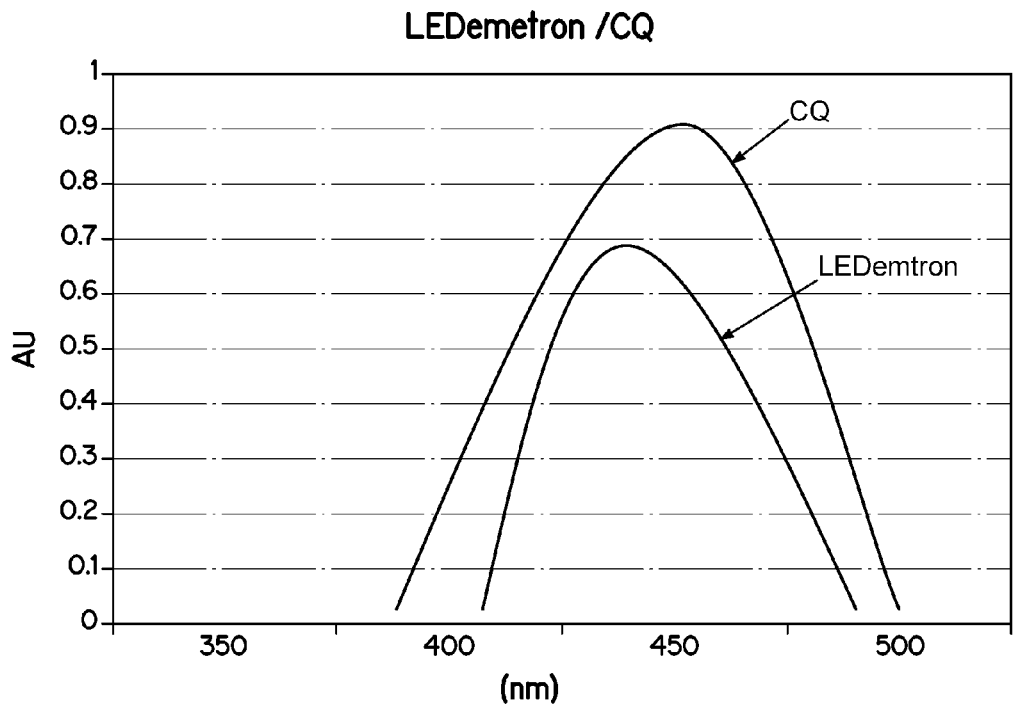
FIG. 11 is a graphical overlay of the light output from an LED light source on the absorption spectra for CQ.
Figure 12:
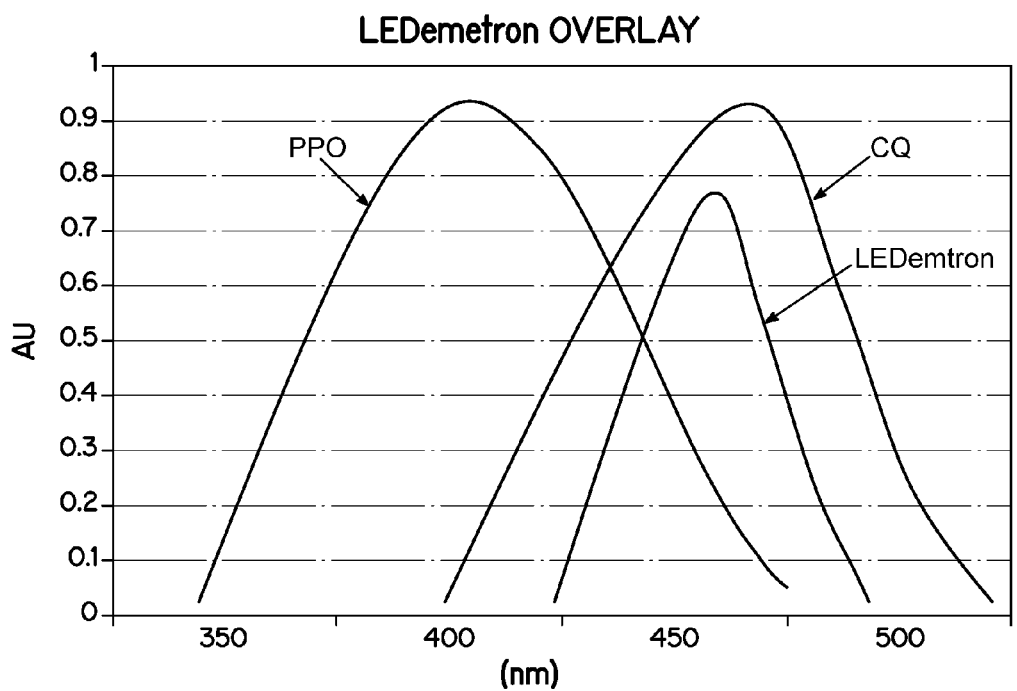
FIG. 12 is a graphical overlay of the light output from an LED light source on the absorption spectra for PPO and CQ.
Figure 13:
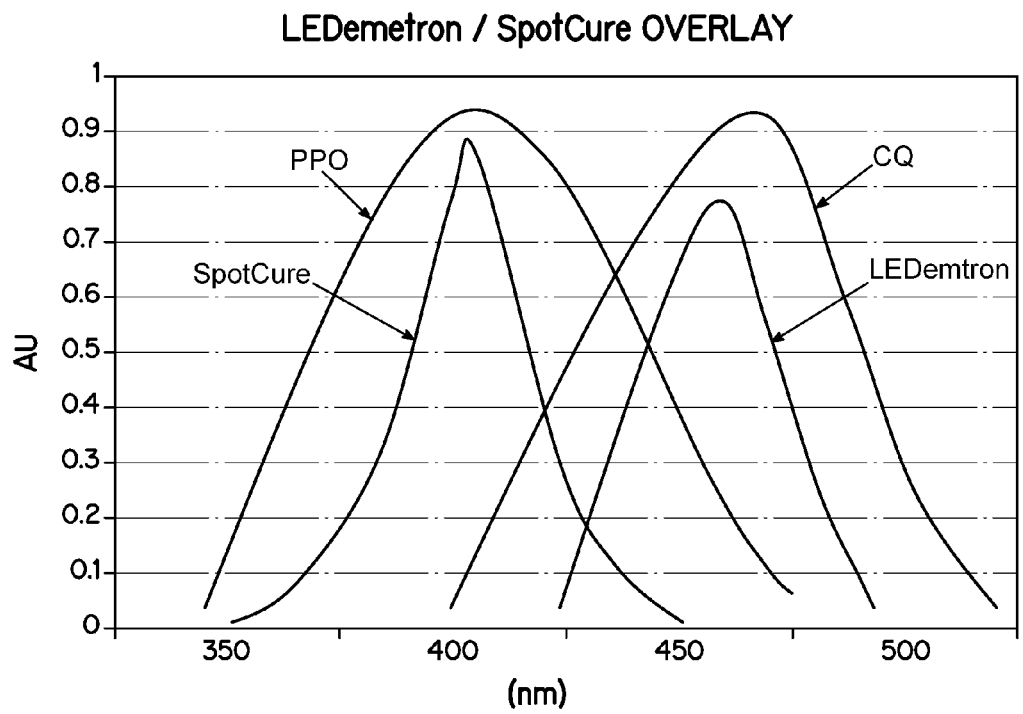
FIG. 13 is a graphical overlay of the light output from two different light sources on the absorption spectra for PPO and CQ.
Figure 14:
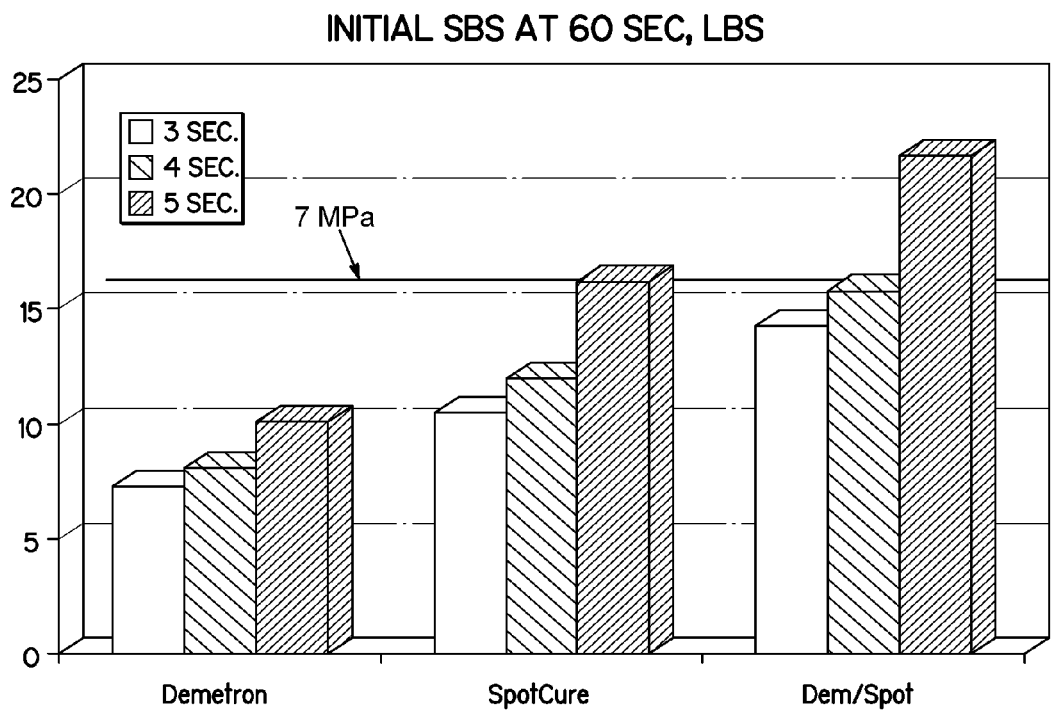
FIG. 14 is a bar graph comparing the initial shear bond strength as a function of time for a formulation of the present invention (Composition A) in the presence of various light sources.

Further with respect to the initiator system of the present invention, the effect of narrow wavelength light is apparent when newer generation battery powered, cordless light emitting diode (LED) curing lights are used. For example, an LEDemetron (cordless battery operated LED dental curing light, Kerr Corporation) is popular and represents the typical wavelength output of commercial LED dental curing lights (452 nm) designed to activate CQ, which is the most common photoinitiator for dental materials. FIG. 11 shows an overlay of the light output from a LEDemetron on the absorption spectra for CQ. Unfortunately, this output is only minimally useful for activation of a phosphine initiator. See overlay in FIG. 12. From this it is apparent that an additional array of lower wavelength LED's is important to better activate the PPO initiator. SpotCure C (UV Process Supply, Inc.) is a LED UV curing light having output maxima at 395 nm. As shown in the overlay in FIG. 13, the SpotCure light output matches well with the PPO absorption curve. SBS testing of Composition A with the different light sources demonstrates the individual contributions of the PPO and CQ sensitizers. For relatively short cure times, the LEDemetron has the ability to set Composition A to low strength primarily through activation of CQ, and SpotCure produces a slightly better result through predominantly PPO activation. However when both the Demetron and SpotCure lights were used simultaneously, the result was a fast, high strength cure about equivalent to the broad wavelength of the Optilux 501 halogen light. See FIG. 14.

Figure 21:
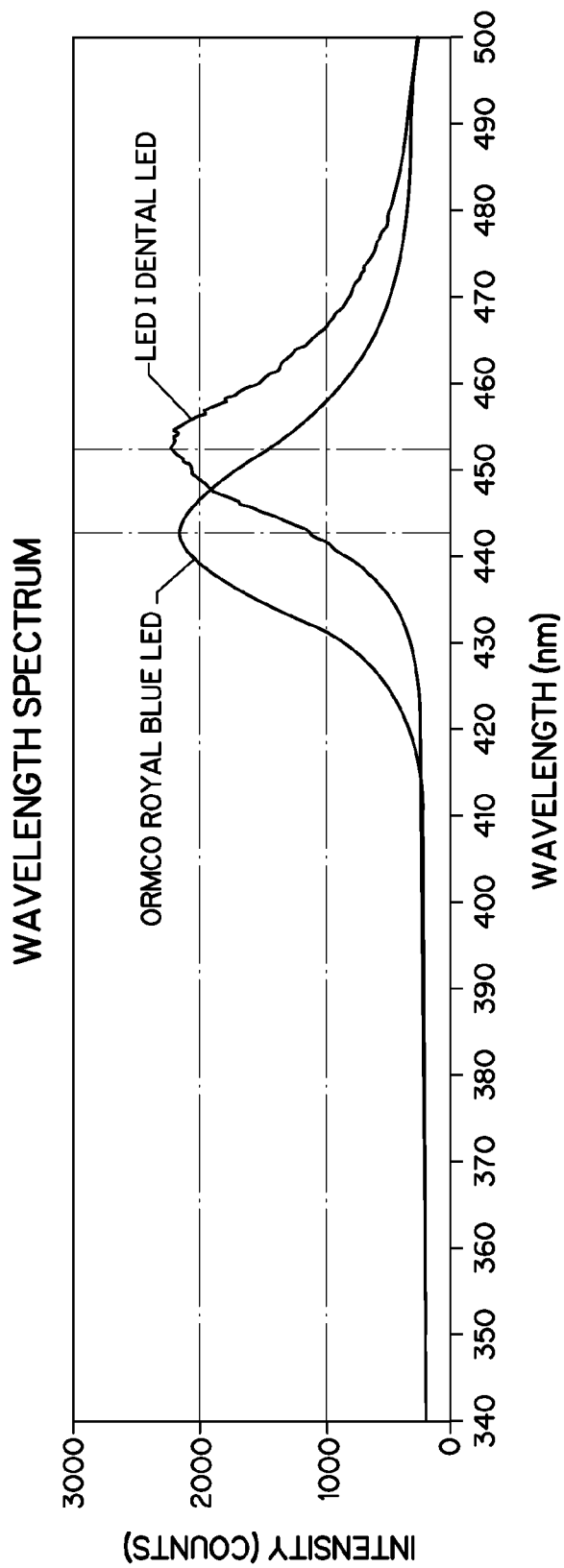
FIG. 21 depicts the wavelength spectra for an LED I dental curing light and a royal blue LED dental curing light.
Figure 22:
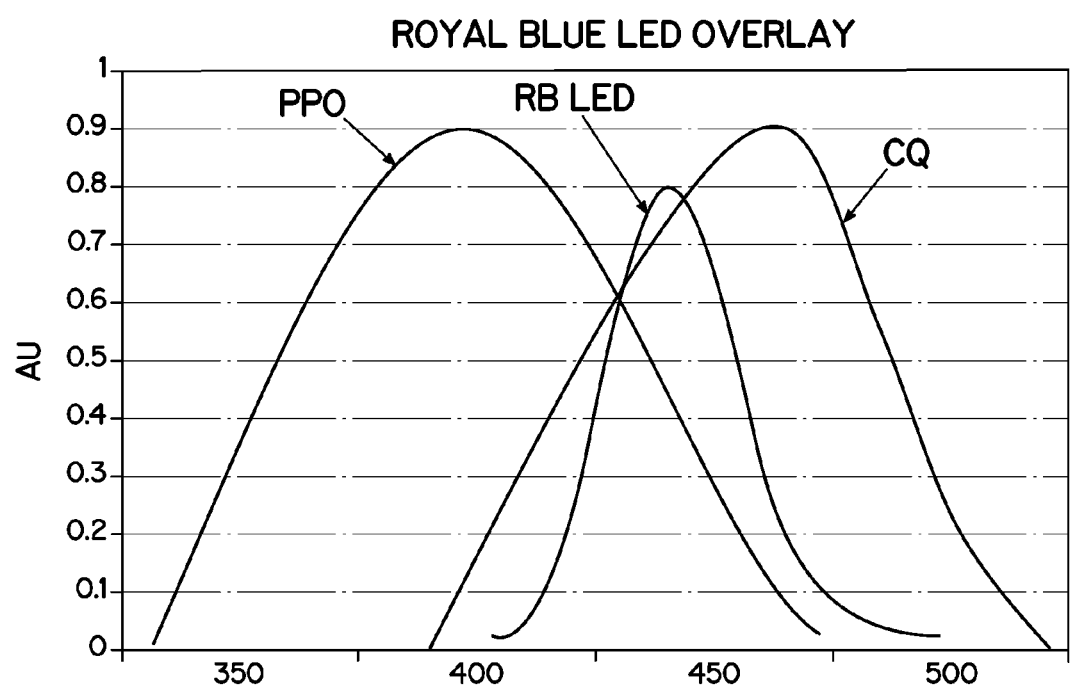
FIG. 22 is a graphical overlay of the light output from a royal blue LED on the absorption spectra for PPO and CQ.

It was discovered that a modified LEDemetron provides excellent curing for compositions of the present invention while not reducing its effectiveness towards the curing of other conventional (CQ binary/ternary) light cured materials. This light utilizes Royal Blue LEDs in place of standard LEDs and is identified as Ormco Royal Blue LED in the FIG. 21 spectra. FIG. 22 shows the approximate overlay of the Royal Blue LED on the CQ and PPO absorption spectra. As shown, the Royal Blue LED has an output maxima at 442 nm. Set forth below are the SBS test results (in lbf) utilizing the immediate strength, 60 second test protocol described above. The same 454-0211 brackets were used.

The second through fourth columns in the table are for Composition A of the present invention.

RB is the Ormco Royal Blue light discussed above.

501 refers to Demetron Optilux 501 halogen dental curing light, and is representative of the majority of corded halogen curing lights currently available having typical output in the 300-550 nm range.

LEDemetron data is representative of the majority of commercial LED dental curing lights currently available as they all generally use the same 452 nm wavelength LEDs targeted for efficient CQ binary/ternary curing.

Columns 5 and 6 exhibit the effectiveness of the Royal Blue light on conventional commercially available adhesives, Enlight (Enl) and Transbond XT (XT). The data for Enlight and Transbond XT is equivalent to using a 501, thus the Royal Blue curing light is an ideal "universal" cordless light. The portability of cordless is popular for easy movement from chair-to-chair in an orthodontic practice. The clinician may upgrade to excellent cordless fast curing of the present invention and at the same time be assured of effective curing of older generation conventional adhesives, band cements, composites, and generally other CQ only based materials that may still be in their office inventory. Values are presented in pounds of force, lbf (MPa).

| Time (sec) | RB | 501 | LEDemetron | RB/Enl | RB/XT |
|---|---|---|---|---|---|
| 2.5 | 20.6 (9.5) | 13.8 (6.3) | 3.2 (1.5) | — | — |
| 5 | 23.4 (10.8) | 25.6 (11.8) | 7.1 (3.3) | — | — |
| 10 | — | — | 16.5 (7.6) | 11.2 (5.1) | 8.6 (4.0) |
| 15 | — | — | — | 22.6 (10.4) | 18.8 (8.6) |

Figure 15:
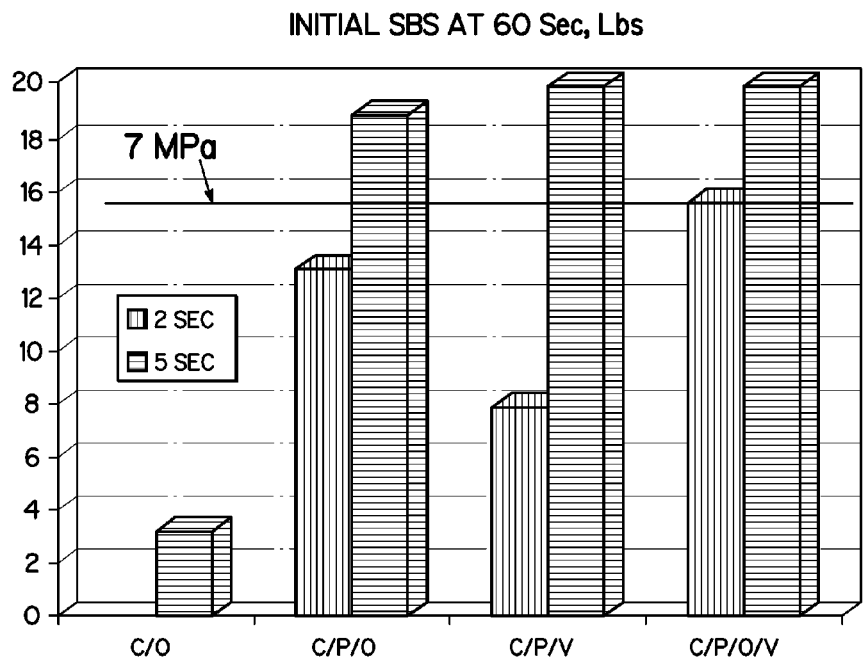
FIG. 15 is a bar graph comparing the initial shear bond strength as a function of time for different sensitizer combinations.

The effect of each initiator component in the quat system of the present invention can be demonstrated. FIG. 15 shows the initial SBS (again using the immediate strength test protocol at 60 seconds described above, and halogen 501 curing light) for compositions containing various combinations of curing initiator components contemplated in the present invention. In FIG. 15, C is camphorquinone, P is phenylbis(2,4,6-trimethyl benzoyl) phospine oxide, O is octyldimethylaminobenzoate and V is 1,1'-azobis(cyanocylohexane). The C and P components are sensitizers, O is a synergistic amine accelerator and V is a catalyst/accelerator. Note the importance of each component. Starting at the left, the C/O bar is a typical binary system and produces the expected low strength result (3 lbf) for short cure time (5 seconds). Moving to the next two bars (C/P/O and C/P/V), it can be seen that adding PPO sensitizer greatly improves the cure strength and may even satisfy inventive W/C requirements. However, only when all four components (C/P/O/V) are present does the strength rise to 7 MPa for very short cure time (2 seconds) in order to maximize the W/C. Thus it is vitally important to balance the concentration of the quat system to maintain long working time and simultaneously maximize nearly instantaneous high strength hardening.

Figure 16:
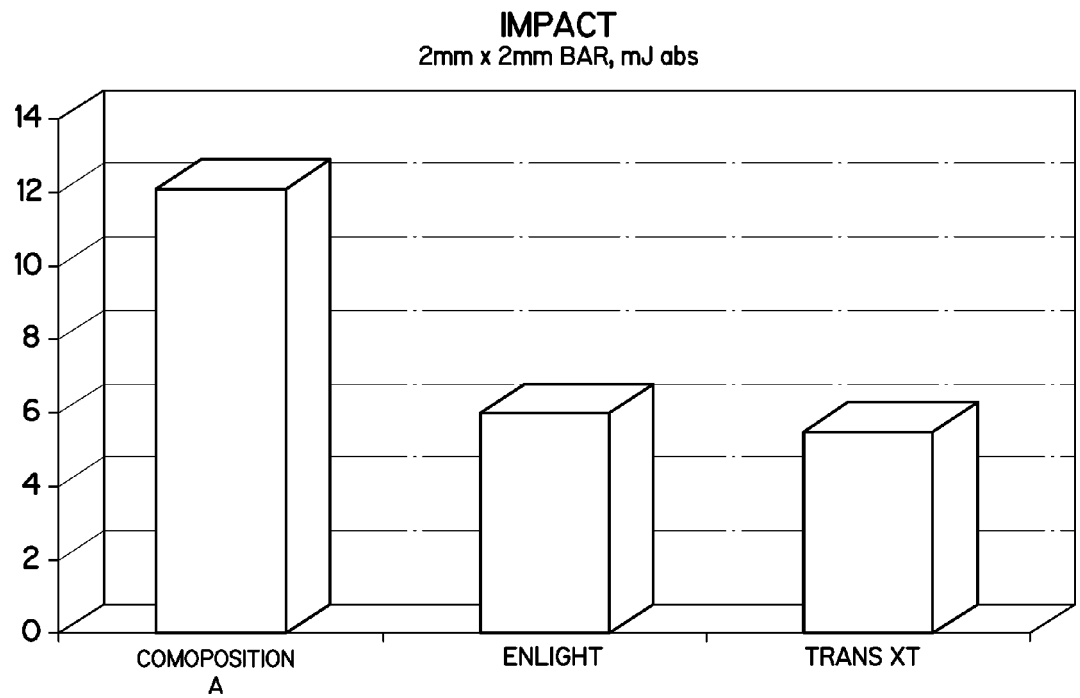
FIG. 16 is a bar graph comparing the impact strength of several samples of orthodontic adhesive compositions.

In the case of orthodontic brackets, assuming the bonding procedure has been completed satisfactorily such that the brackets are attached to the patient's teeth in the desired position and the archwire is ligated, there is an improved probability that the brackets will stay attached, even under trauma situations, if the adhesive layer is toughened (versus brittle, which is typical of current market leading materials, i.e., Transbond XT, Enlight). There are several methods of toughening a composite both from the resin matrix approach, and also from the reinforcement aspect as is well known in the art. In the compositions of the present invention, including Composition A, the resin matrix has been designed to absorb impact energy while the glass filler provides strength. This is accomplished by using a methacrylated urethane resin monomer designed for the purpose as described in U.S. Pat. No. 4,554,336, the disclosure of which is incorporated herein by reference. Under pendulum impact loading (Ormco custom designed instrumented "Izod" type energy measuring device) the invention clearly outperforms the current market leaders. FIG. 16 shows a comparison of impact toughness for Composition A versus Enlight and Transbond XT.

Figure 17:
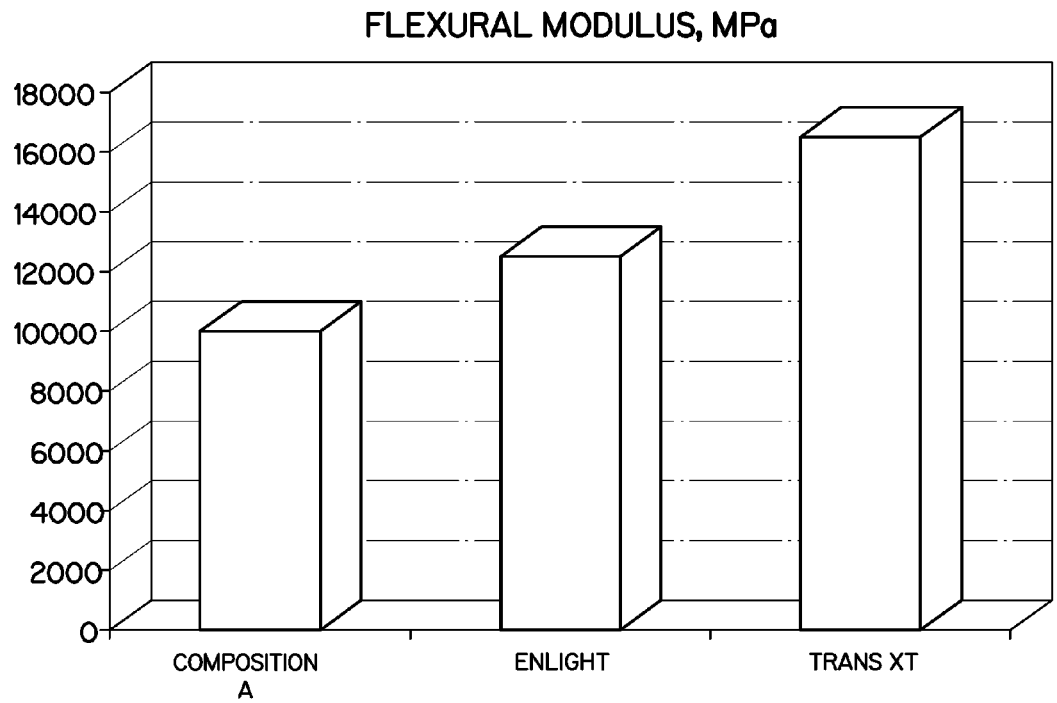
FIG. 17 is a bar graph comparing the flexural modulus for several orthodontic adhesive compositions.
Figure 18:
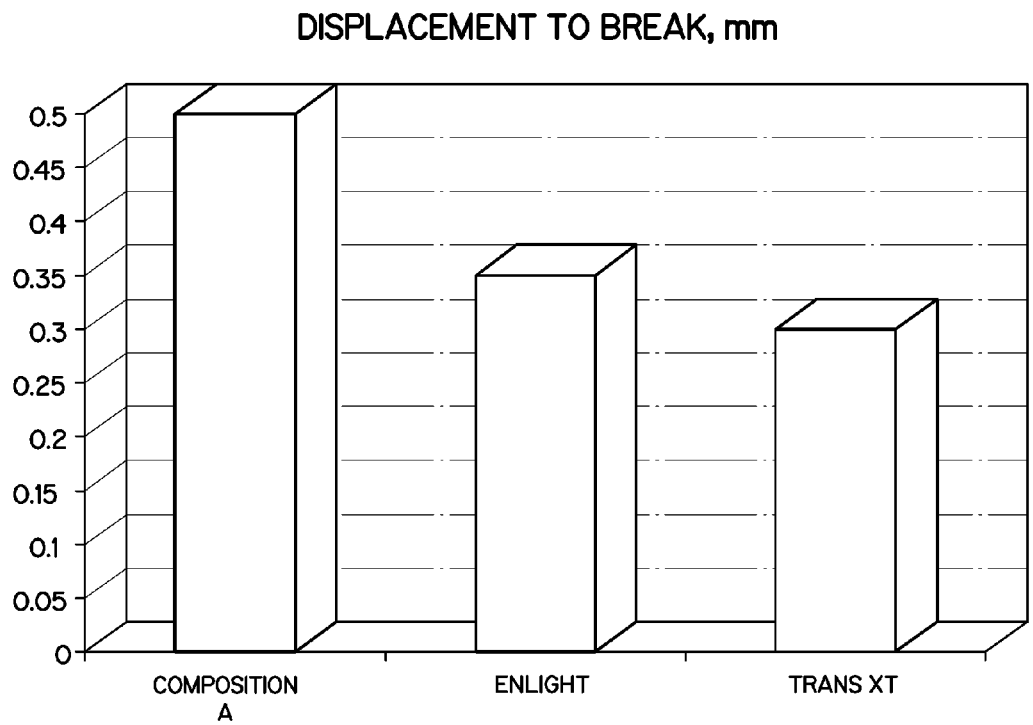
FIG. 18 is a bar graph comparing the displacement to break, in millimeters, for several orthodontic adhesive compositions.
Figure 19:
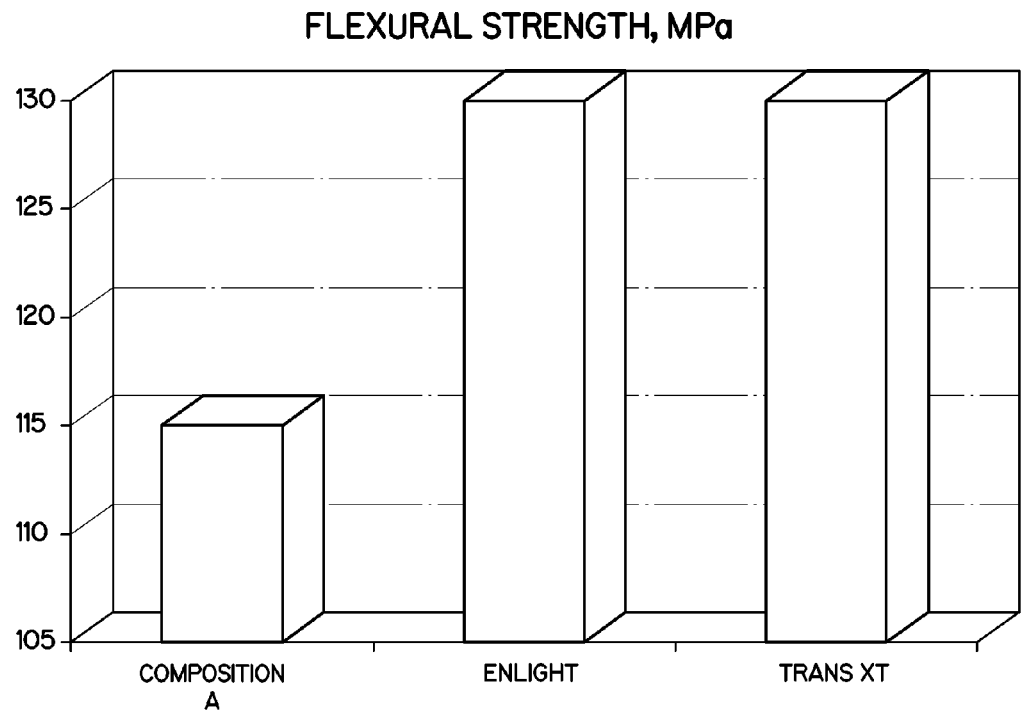
FIG. 19 is a bar graph comparing the flexural strength for several orthodontic adhesive compositions.

The toughening additive yields other mechanical properties that differ significantly versus leading competitive materials. The emphasis is on maintaining a high strength material, but having slightly lower modulus and higher displacement such that the mass can flex to some degree. The tough and flexible characteristic is particularly important to fend off high speed (high strain rate) events, whereby glassy materials will shatter under relatively light loads (compare a BB dropped versus firing out of a gun onto a window pane). For example, envision a situation where a sudden impact could occur if, while chewing ice, the teeth slip jamming hard ice against the bracket at high speed. Brittle materials that cannot deflect will tend to catastrophically fail, whereas an acceptably strong material that also has the ability to elongate while absorbing and dissipating energy will reduce the possibility of bond failure (now substitute the window glass for a resilient urethane bullet proof sheet). Relative comparisons are shown in FIGS. 17-19.

The resiliency (area under the Tensile stress-strain curve) is another measure of a material's ability to absorb energy prior to rupture. Composition A was compared to a previously completed study under the same experimental procedure done by a university student, included by reference herein (Proctor DL, Fracture properties of different orthodontic bonding materials, Loma Linda University graduate school Masters Thesis, June 2001). The resiliency of Composition A was found to be higher than all, and have the best overall performance. The following table exemplifies the marked enhancement Composition A offers. The means are reported for n=5.

| Adhesive Name (Mfg) | Resilience (MPa) | Stress (MPa) | Strain@ Break (%) | Modulus (MPa) |
| --- | --- | --- | --- | --- |
| Composition A | 0.81 | 81.9 | 2.00 | 4566 |
| Enlight (Ormco) | 0.32 | 52.4 | 1.19 | 4555 |
| Transbond XT (3M) | 0.46 | 65.8 | 1.35 | 5102 |
| Concise (3M) | 0.46 | 62.0 | 1.47 | 4695 |
| Light Bond (Reliance) | 0.80 | 87.5 | 1.79 | 5299 |
| Phase II (Reliance) | 0.51 | 66.1 | 1.49 | 4831 |
| Eagle No-drift (American Ortho) | 0.25 | 46.3 | 1.07 | 4591 |
| Fuji LC 0.46 (Fuji) | 0.23 | 37.7 | 1.18 | 3562 |
| Ideal (GAC) | 0.31 | 50.7 | 1.14 | 4660 |

Figure 20:
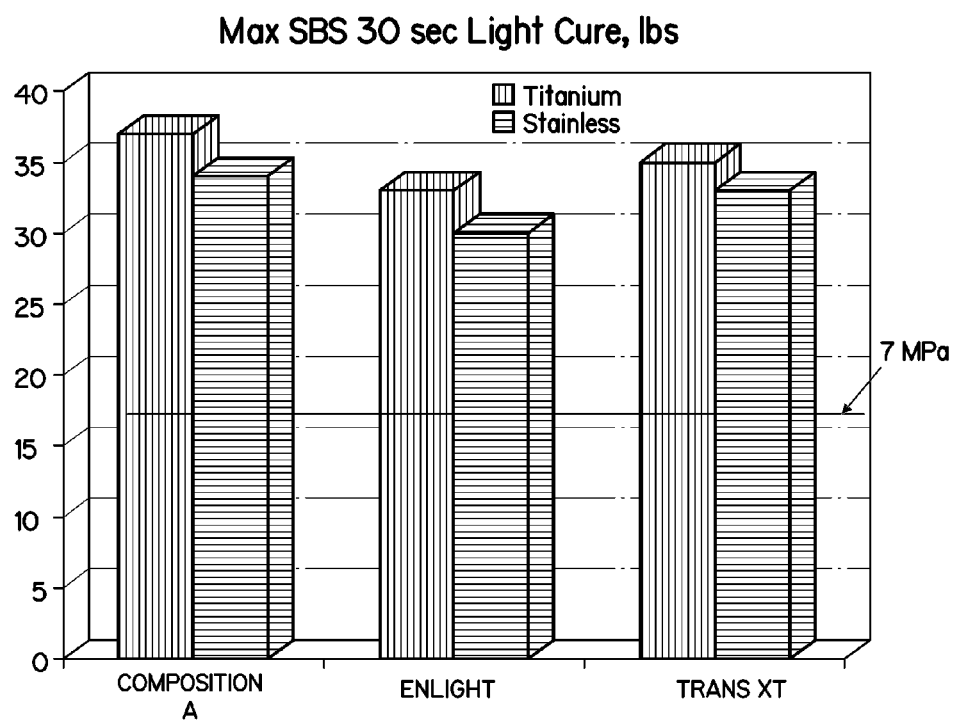
FIG. 20 is a bar graph comparing the maximum shear bond strength after 30 seconds of light curing for several orthodontic adhesive compositions.

While Composition A is intended to be useful for all bracket materials, i.e. metal, ceramic, and plastic, it is particularly targeted at the metal bracket segment. Thus, another key design characteristic is metal adhesion. The urethane resin previously described for improved impact properties was also designed to have improved attraction to metal making it particularly useful for this invention. The '336 patent describes the preferential bonding to metal surfaces through the cyano moieties of the urethane. To take full advantage of this property, a reasonable approach is to improve the wetting characteristics so that the cyano moieties are in close proximity of the bonding surface. It is important to note that a few manufacturers and/or some dental offices alter the bracket base topography to increase the surface area. Some simply sandblast the bonding surface so that it is roughened and pitted. Ormco provides a metallic particulate that is sintered to the mesh wires and backing pad. The performance of these micro-retention provisions is best enhanced if the adhesive can intimately flow in and around these physical features of the bonding base. Because the compositions of the present invention, and particularly Composition A, are heavily filled high viscosity pastes similar to the consistency of peanut butter, various internal wetting agents/surfactants may be useful to help the paste to flow into the micro-cavities, thus producing enhanced mechanical retention. The term wetting agent/surfactant as used herein refers to those compounds that would serve to reduce the contact angle of the resin matrix on a bonding surface. Common surfactants such as the Tweens and Spans may be useful but are non-participants in the setting reaction, and, as spectators may undesirably reduce some properties, e.g., act as plasticizer that would lead to lower strength. U.S. Pat. No. 6,387,982 describes polymerizable surfactants that may participate in the setting reaction such that other key physical properties are not degraded. Similarly, some commercial resins are useful for improving the matrix contact. While the contact angle was not specifically measured for contemplated compositions, the key surface-active components of the present invention when compared to various prior art would support the overall improved bond strength results noted. U.S. Pat. No. 5,362,769 describes the use of hydrophilic comonomers for the purpose of producing a high degree of surface wetting in orthodontic adhesive compositions. Some exemplary preferred reactive polymerizable wetting agents include hydroxyethyl methacrylate, hydroxypropyl methacrylate, methylmethacyrlate, methacrylic acid, and glycerol dimethacrylate. On a molecular level, proper wetting allows the resin to intimately contact a high proportion of the metallic bonding surface so that preferred chemical attractions at bond-length distances can result, e.g. the cyano moieties of the urethane noted above. Further, this is equally important for reactive multi-functional bond-enhancing co-monomers, e.g., 4-methacyloxyethyl trimellitic annhydride, pyromelletic glycol dimethacrylate, glycidyl methacrylate, 2-(methacryloxy)ethyl phenyl hydrogen phosphate, and glycerophosphate dimethacrylate, that may be included to incrementally boost bond strength. Also, in certain circumstances various silane surface active adhesive resins may be useful, e.g., when a bonding base is naturally silica-rich, or silica-enhanced, e.g., by the process of deposition or embedding. Urethane resins, together with surfactant and/or wetting agents and bond enhancing comonomers likely contribute to the significantly and consistently higher bond strengths, including final maximum strength when compositions of the present invention, including Composition A, are used to bond titanium and stainless steel brackets. FIG. 20 shows the maximum SBS (in lbf) after 30 seconds of light curing with an Optilux 501.

To achieve high strength, high reactivity, and the ability to adjust for particular handling characteristics that are desired by orthodontic practitioners, careful consideration of choice of resin and filler components is required. Many commercial resins that are well known in the art are suitable, preferably polymerizable components that are monomer, oligomer or polymer having free-radically polymerizable groups. Exemplary examples are disclosed in U.S. Pat. No. 6,126,922 which have the reactive acrylate and methacrylate functionality. When combined with the inventive quat system, most any reasonably reactive mono or poly acrylate or methacrylate composition will exhibit the desirable W/C character. As an example, a preferred "base" resin composition may consist of:

| Component | Description | Wt % |
|---|---|---|
| Bis GMA | Bisphenol A diglycidyl ether dimethacrylate | 5-20 |
| EOTMPTA | Ethyloxylated trimethylopropane triacrylate | 5-20 |
| EBADMA | Ethoxylated bisphenol A dimethacrylate | 15-30 |
| TEGDMA | Triethyleneglycol dimethrylate | 40-60 |

The filler selection plays an important role for achieving desirable handling characteristics, strength, and other key physical properties. A filler or combination of fillers may be chosen from any of the types or sizes well know in the art including but not limited to ground glass, fumed or precipitated silica, nano-particle, and prepolymerized composite types. As with most other competitive materials, these compositions have friendly handling characteristics, syringe/unit delivery properties, and long shelf life. Composition A is summarized as follows:

| Component | Description | Weight % |
|---|---|---|
| Base Resin | Table above | 4.7 |
| GMA | Glycidyl methacrylate | 0.9 |
| GDM | Glycerol dimethacrylate | 0.9 |
| MUR | Methacrylated Urethane resin | 17.3 |
| CQ | Camphorquinone | 0.05 |
| PPO | Bis(2,4,6-trimethylbenzoyl)-phenylphosphineoxide | 0.6 |
| V88 | 1,1'-Azobis(cyanocyclohexane) | 0.2 |
| ODMAB | Octyldimethylaminobenzoate | 0.07 |
| BHT | 2,6-di-(t-butyl)-4-methylphenol | 0.01 |
| Colorant | leuco dye | 0.02 |
| Filler | Silica-based glass | balance |

As mentioned, compositions of the present invention are useful for bonding all types of bracket configurations and materials, i.e., metal, ceramic, and plastic/composite. Composition A is targeted for bonding metallic articles, particularly stainless steel and titanium brackets. Composition A may be used for aesthetic (clear) brackets, but it is primarily recommended for metal brackets. This is partly due to its color, which can be a highly saturated hue under cold (less than 30° C.) conditions in the mouth, but also its very high strength, which is beyond what is required for ceramic brackets.

The improved W/C ratios of the compositions of the present invention are also suited for aesthetic/clear plastic and ceramic brackets. In this case, the design criteria focuses on high bond strength to polycarbonate composite bracket material, and at the same time a limited (maximum ceiling) bond strength for ceramic brackets.

Typically in the bonding of composite (plastic) brackets, a primer must be applied to the plastic bonding surface of the bracket to effect a pseudo solvent-welding/chemical affinity, and at the same time provide pendant acrylate chemistry to couple with the bonding adhesive. This primer step is not required when utilizing Composition B of the present invention because it includes a unique combination of bond enhancing additives, some of which have previously been described, but may preferably include methylmethacrylate, ethyl methacrylate, methacrylic acid, glycidyl methacrylate, butyl methacrylate and tetrahydrofurfuryl methacrylate. The bond-enhancing effect to plastic brackets essentially eliminates the need to prime the base with a separate dedicated coupling agent, thus eliminating a very time consuming, technique sensitive, and added cost step. When using Composition B to bond plastic brackets, simply place the adhesive directly on the plastic bracket base and proceed to cure with an Optilux 501 curing light.

For bonding ceramic brackets, the excessive bond strengths typical of ceramic brackets should be addressed. It is believed that the ideal shear bond strength for a ceramic bracket (e.g., Ormco Ice) is 15-20 MPa. Sometimes SBS values on the order of 30 MPa or more are achieved. Clinicians are sensitive to the forces that may fracture enamel, and when they come across these high strength bonds during a planned de-bracketing, the article must be removed by some other time consuming, difficult and/or uncomfortable means, e.g., grinding it off with a diamond burr. By varying the ratio of certain resin components in the compositions of the present invention, particularly Composition B, the inherent ceiling bond strength of the adhesive resin may be controlled such that a bracket under debonding forces will not load above a predetermined threshold value; in other words, the adhesive will fail cohesively before excessively high forces are reached. An alternative or synergistic method to accomplish a similar effect is through the partial, or up to 100% use of low strength filler components, e.g., pre-polymerized composite filler, in which case the strength of the filler can be precisely controlled through the use of a designed resin matrix, and type and loading of filler. In any case, the compositions of the present invention, particularly Composition B, provide high strength bonding for polycarbonate brackets, but limited maximum bond strength for ceramic brackets. These compositions further possess the proper handling characteristics and the highly desirable W/C ratios discussed previously.

The Composition B formulation is set forth in the table below. As stated, Composition B makes use of the same quat initiator system as Composition A, and the base resin is similar, thus desirable W/C's are achieved. However, Composition B may include strength-diluting resins, e.g., oligomers of inherent low strength such as olefinic, styrenic, amides, acrylic, urethane and various copolymers. Generally the reduced strength effect is best achieved when these oligomers are reactive, i.e., acrylate or methacrylate functional. Of particular interest are polyurethane oligomers, e.g., those of the '336 patent can be tailored accordingly to provide backbone structures that will yield lower strength composites when used in appropriate concentrations. Other commercially available materials may be suitable, e.g., Polymer Systems Corp., Orlando, Fla. produces a wide variety of urethane oligomers. A preferred Polymer Systems oligomer, M143V, is an aliphatic (color stability), long-chain soft-segment (low strength, high ductility), and polyfunctional methacrylic functional urethane resin. In Composition B, a portion of the higher strength methacrylated urethane resin of Composition A is replaced with M143V. By adjusting the ratio, the ceiling strength of the adhesive can be controlled well. A range of formulations that sets the maximum SBS at any value between about 8 and 20+/−2 MPa can be achieved. In the specific formulation of Composition B, the SBS is adjusted to about 15 MPa, which is desirable for use with Ormco's Inspire ICE ceramic bracket. This also achieves a high tensile bond strength (TBS, which is the preferred mode used to measure adhesion of plastic brackets) for Ormco's Damon 3 polycarbonate brackets. SBS for ICE below about 12 MPa becomes unacceptable for Damon 3 TBS. TBS above about 10 MPa is desirable.

| Component | Description | Weight % |
|---|---|---|
| Base Resin | Table above | 3.9 |
| GDM | Glycidyl methacrylate | 0.8 |
| GMA | Glycerol dimethacrylate | 3.9 |
| MUR | Methacrylated Urethane resin | 8.4 |
| M143V | Methacrylated Urethane resin | 5.0 |
| ODMAB | Camphorquinone | 0.06 |
| Camphorquinone | Bis(2,4,6-trimethylbenzoyl)-phenylphosphineoxide | 0.04 |
| PPO | 1,1'-Azobis(cyanocyclohexane) | 0.5 |
| V-88 | Octyldimethylaminobenzoate | 0.2 |
| BHT | 2,6-di-(t-butyl)-4-methylphenol | 0.01 |
| colorant | leuco dye | 0.31 |
| Filler | Silica-based glass | Balance |

The adhesive compositions of the present invention may be used in direct bonding procedures, the methodology of which is known in the art. By way of example, the general procedure is provided as follows: tooth preparation is performed by etching for approximately 30 seconds per tooth, rinsing thoroughly for a minimum of 5 seconds per tooth with a forceful air/water spray and suction using a high-speed evacuator; then dry the etched enamel with clean, dry air to a dull, frosty appearance. Next, apply a bonding sealant to the prepared tooth. Then extrude a small amount of Composition A (or other suitable composition of the present invention) paste onto the bracket pad. Next, (A) immediately place bracket, (B) position, (C) press gently, (D) remove excess adhesive. Light cure utilizing a halogen light: 5 seconds for all bracket types 10 seconds for molar tubes. These times are also applicable when using the Ormco Royal Blue LED.

As an alternative to direct bonding, indirect bonding is a technique that is used in about 15% of initial bondings. Precision placement is one advantage of indirect bonding, and other advantages include patient comfort and chair time savings. The initial appointment is short; impressions of the malocclusion are taken, and the patient is released. Stone models of the patient's teeth are produced from the impression. Brackets are set-up on the model by the clinician and/or staff, or often by a specialized outside lab: in either case the set-up is painstakingly perfected under unlimited time conditions and often assisted by computer-aided tools, in an effort to produce the most effective end results. When the brackets are satisfactorily set in exacting position, a clear plastic tray is formed over the arch having brackets attached. The tray with brackets imbedded is then separated from the model. The patient is scheduled for a bonding appointment. Once seated with teeth properly etched and prepared, bonding adhesive of the present invention is applied to the bracket bases in the tray, then the tray with adhesive-coated brackets is fitted on the patient's teeth. The adhesive is cured and the tray is removed. In this procedure, the patient comfort is improved since seating of the tray bonds several brackets in shortened time as compared with direct bonding, and with minimal discomfort. More importantly, the brackets are positioned perfectly so the treatment progresses with less difficulty to a more desirable finish, usually with less appointments needed, and in shorter overall time. The adhesives of the present invention, which quickly set to high strength, are highly advantageous for the indirect bonding technique.

Orthodontic adhesives typically are either self/chemical cure A/B types, or light cure adhesives. For indirect bonding using self-cure adhesives, one component is painted on the bracket side and the other is painted on the tooth side. The act of seating the tray of brackets begins the mixing that initiates the chemical (reduction-oxidation) reaction. Care must be taken not to physically disturb the setting reaction, but at the same time intimate contact is required so that the bracket bases are properly seated and the chemistry is at peak efficiency. In practice, several fingers are placed at key locations on the tray to coax brackets to set at the proper locations. The curing takes place over a period of several minutes and after approximately 10 minutes the tray is removed. For indirect bonding using a light cure adhesive, a dollop of the adhesive is placed on each bracket base and the tray is seated. The clinician carefully lights each bracket, one at a time, through the clear tray. The cure time per bracket is about 60 seconds for the best materials. Trays are generally placed in quadrants, thus for a 5 bracket tray (central, lateral, cuspid, bicuspid, $2^{nd}$ bicuspid) the time elapsed is about 5 minutes. Similar to, but possibly a bit faster than self-cure.

As much as these indirect bonding techniques seem like tedious and costly chair time procedures, direct bonding is not as accurate, takes longer chair time, and in the long run is not as effective since it may require wire bends, or worse, bracket re-position to more desirably finish the case. However, the compositions of the present invention have the advantage of reducing the curing times significantly, on the order of 5 to 10 seconds per bond. Thus, bonding of multiple brackets in a quadrant tray can be completed in less than 1 minute, such that the entire upper and lower arch requires less than 4 minutes of light curing versus 20 minutes using conventional adhesives. As previously discussed, about 7 MPa is considered a successful initial bond strength when bonding orthodontic brackets. This holds true for indirect bonding because the forces to remove a tray can sometimes be relatively high and/or multi-modal, and subsequent wire tie-in follows immediately. A tray is typically 2 layers composed of a soft pliable inner layer and a rather rigid outer layer, and should be as clear as possible particularly for light cured procedures. The tray inner layer may be ethylene vinyl acetate, a clear thermoformed plastic that molds itself well over the details of the bracket so that it cannot change position, which is essential for accurate placement. Alternatively, the inner tray can be a clear polysiloxane or silicone-type material that is hand molded to the bracket details and is allowed to cure. The outer layer is a stiffer, clear, thermoformed plastic, e.g., acrylic, or polyester, that holds the shape of the arch so that several teeth can be bonded to simultaneously without the tray flopping about. Unfortunately, light exiting a curing light guide tip (except laser) is non-collimated and multi-directional so energy fall-off is exponential as the distance is increased and/or transmittance is decreased. Even when the materials are kept to minimum thickness, laminate and even single-piece trays can result in the curing light guide tip to be in rather poor proximity to the bonding adhesive, often 5 or more mm away. Additionally, the resultant tray assembly is generally translucent, not transparent, so there is a further reduction of available light energy at the bond interface. As a result, the cure time for current adhesives must be increased to compensate. For known adhesives that normally require 15 seconds for direct bonding, the time must be increased to 60 or more seconds to attain an immediate shear bond strength of 7 MPa. However, compositions of the current invention maintain high sensitivity to available curing light such that short cure times are still achieved. The following table further exemplifies the benefits of the compositions of the present invention. The data in the table compares the shear bond strength of indirectly bonded stainless steel brackets for Composition A versus a popular conventional light curing bonding adhesive, and also compares this data to the direct bonding technique. The indirect bonding trays consisted of an ethylene vinyl acetate inner layer holding the brackets, and a rigid acrylic outer layer. Etched and dry bovine teeth were primed with Ormco Ortho Solo® sealant. Once the tray was seated, curing was accomplished using an Optilux 501 curing light for the times (seconds) noted. Immediate SBS in MPa was measured within 2 minutes after light cure on an Instron model 4467 at strain rate 2 mm/min.

| Cure time | Indirect Bond | | Direct bond | |
|---|---|---|---|---|
| | Composition A | 3M Transbond XT | Composition A | 3M Transbond XT |
| 5 seconds | 7.1 MPa | — | 8.0 | — |
| 10 | | — | | 4.5 |
| 15 | | 2.2 | | 6.7 |
| 30 | | 3.4 | | |
| 40 | | 5.6 | | |
| 60 | | 6.8 | | |

While the foregoing description has set forth preferred embodiments of the present invention in particular detail, it must be understood that numerous modifications, substitutions and changes can be undertaken without departing from the true spirit and scope of the present invention as defined by the ensuing claims. The invention is therefore not limited to specific embodiments as described but is only limited as defined by the following claims.

What is claimed is:

1. A single component light-curable orthodontic adhesive comprising:
   a curable resin monomer component, said curable resin monomer component comprising at least bisphenol A diglycidyl ether dimethacrylate, ethoxylated trimethylopropane triacrylate, ethoxylated bisphenol A dimethacrylate, and triethylene glycol dimethacrylate;
   a quaternary curing initiator system comprising:
      camphorquinone,
      bis(2,4,6-trimethylbenzoyl)-phenylphosphine oxide,
      octyldimethylaminobenzoate, and
      1,1'-azobis(cyanocyclohexane); and
   filler,
   wherein the single paste light-curable orthodontic adhesive has a working time (W) to curing time (C) ratio (W/C) of at least 10 to 30,
   wherein said working time is expressed as a multiple of a five second interval that is visually determined as a point at which an approximately 2 mm×2 mm extruded sample of the single component light-curable orthodontic adhesive sufficiently hardens to a crusty consistency and undergoes a brittle fracture when cut in approximately 2 mm sections under a halogen operatory exam light positioned to provide 10,000±50 lux at the extruded sample on a white background, and
   wherein said curing time is a duration of exposing the single component light-curable orthodontic adhesive to a curing light that is necessary to effect a shear bond strength greater than 7 MPa within 60 seconds after the single component light-curable orthodontic adhesive is applied to an etched and sealed bovine tooth.

2. The orthodontic adhesive of claim 1, wherein said curable monomer component further includes at least one of the following: pyromellitic glycol dimethacrylate, glycidyl methacrylate, and glycerol dimethacrylate.

3. The orthodontic adhesive of claim 1, further comprising a colorant.

4. The orthodontic adhesive of claim 3, wherein the colorant includes at least one reversible dye.

5. The orthodontic adhesive of claim 4, wherein the reversible dye is thermochromatic.

6. The orthodontic adhesive of claim 5, wherein the reversible, thermochromatic dye has a readily visible, non-tooth colored color below its clearing temperature and is generally tooth colored at body temperature.

7. The orthodontic adhesive of claim 1, further comprising a resin toughening component.

8. The orthodontic adhesive of claim 7, wherein the resin toughening component is a methacrylated urethane resin.

9. The orthodontic adhesive of claim 8, wherein the resin toughening component is an acrylic terminated polyurethane.

10. The orthodontic adhesive of claim 1, wherein the quaternary curing initiator system consists essentially of camphorquinone, bis(2,4,6-trimethylbenzoyl)-phenylphosphine oxide, octyldimethylaminobenzoate and 1,1'-azobis(cyanocyclohexane).

11. The orthodontic adhesive of claim 1, wherein the W/C ratio is at least 12.

12. The orthodontic adhesive of claim 1, wherein the W/C ratio is at least 14.

13. The orthodontic adhesive of claim 1, wherein the W/C ratio is at least 20.

14. The orthodontic adhesive of claim 1, wherein the curable resin monomer component comprises at least:
   5 wt % to 20 wt % of bisphenol A diglycidyl ether dimethacrylate,
   5 wt % to 20 wt % of ethoxylated trimethylopropane triacrylate,
   15 wt % to 30 wt % of ethoxylated bisphenol A dimethacrylate, and
   40 wt % to 60 wt % of triethylene glycol dimethacrylate,
   wherein wt % is based on the total weight of the curable resin monomer component.

15. The orthodontic adhesive of claim 1, wherein the curing light is a halogen curing light having an 850 Mw/cm$^2$ output in the 400-505 nm range.

16. The orthodontic adhesive of claim 1, wherein the quaternary curing initiator system comprises:
   0.04 wt % to 0.05 wt % camphorquinone,
   0.5 wt % to 0.6 wt % bis(2,4,6-trimethylbenzoyl)-phenylphosphine oxide,
   0.06 wt % to 0.07 wt % octyldimethylaminobenzoate, and
   0.2 wt % 1,1'-azobis(cyanocyclohexane), wherein wt % is based on the entire weight of the single component light-curable orthodontic adhesive.

17. A single component light-curable orthodontic adhesive comprising:
- a curable resin monomer component, said curable resin monomer component comprising at least bisphenol A diglycidyl ether dimethacrylate, ethoxylated trimethylopropane triacrylate, ethoxylated bisphenol A dimethacrylate, and triethylene glycol dimethacrylate;
- a quaternary curing initiator system comprising: camphorquinone, bis(2,4,6-trimethylbenzoyl)-phenylphosphine oxide, octyldimethylaminobenzoate, and 1,1'-azobis(cyanocyclohexane); and
- filler,
- wherein the single component light-curable orthodontic adhesive will not harden to a crusty consistency for about 70 seconds to about 100 seconds when exposed to a halogen operatory exam lamp positioned at a distance providing 10,000±50 lux output for an approximately 2 mm×2 mm×20 mm extruded sample of the adhesive on a white background; and wherein the single component light-curable orthodontic adhesive is capable of exhibiting a shear bond strength, when applied to an etched and sealed bovine tooth, of greater than 7 MPa within 60 seconds after light curing for a duration of 2 seconds to 5 seconds, as measured using a halogen curing light having an 850 mW/cm$^2$ output in the 400-505 nm range to irradiate the adhesive applied to an etched and sealed bovine tooth.

18. A single component light-curable orthodontic adhesive comprising:
- a curable resin monomer component including more than one different curable resin monomer;
- a quaternary curing initiator system comprising: camphorquinone, bis(2,4,6-trimethylbenzoyl)-phenylphosphine oxide, octyldimethylaminobenzoate, and 1,1'-azobis(cyanocyclohexane); and
- filler,
- wherein the single paste light-curable orthodontic adhesive has a working time (W) to curing time (C) ratio (W/C) of at least 10 to 30,
- wherein said working time is expressed as a multiple of a five second interval that is visually determined as a point at which an approximately 2 mm×2 mm extruded sample of the single component light-curable orthodontic adhesive sufficiently hardens to a crusty consistency and undergoes a brittle fracture when cut in approximately 2 mm sections under a halogen operatory exam light positioned to provide 10,000±50 lux at the extruded sample on a white background,
- wherein said curing time is a duration of exposing the single component light-curable orthodontic adhesive to a curing light that is necessary to effect a shear bond strength greater than 7 MPa within 60 seconds after the single component light-curable orthodontic adhesive is applied to an etched and sealed bovine tooth,
- wherein said curable monomer component includes at least four of the following:
- bisphenol A diglycidyl ether dimethacrylate, ethoxylated bisphenol A dimethacrylate, ethoxylated trimethylopropane triacrylate, pyromellitic glycol dimethacrylate, triethylene glycol dimethacrylate, glycidyl methacrylate, and glycerol dimethacrylate, and
- wherein the curable resin monomer component comprises at least
  - 5 wt % to 20 wt % of bisphenol A diglycidyl ether dimethacrylate,
  - 5 wt % to 20 wt % of ethoxylated trimethylopropane triacrylate,
  - 15 wt % to 30 wt % of ethoxylated bisphenol A dimethacrylate, and
  - 40 wt % to 60 wt % of triethylene glycol dimethacrylate, wherein wt % is based on the total weight of the curable resin monomer component.

* * * * *